United States Patent
Watanabe et al.

(10) Patent No.: US 6,919,292 B2
(45) Date of Patent: Jul. 19, 2005

(54) TRANSITION METAL COMPOUND, COORDINATIVE COMPOUND, CATALYST FOR POLYMERIZATION OF OLEFIN, AND PROCESS FOR POLYMERIZATION OF OLEFIN USING THE CATALYST

(75) Inventors: Makoto Watanabe, Yokkaichi (JP); Takashi Okada, Kuwana (JP); Morihiko Sato, Yokkaichi (JP); Satoshi Hamura, Yokkaichi (JP); Masao Tanabiki, Yokkaichi (JP)

(73) Assignee: Tosoh Corporation, Shinnanyo (JP)

( * ) Notice: Subject to any disclaimer, the term of this patent is extended or adjusted under 35 U.S.C. 154(b) by 281 days.

(21) Appl. No.: 10/022,772

(22) Filed: Dec. 20, 2001

(65) Prior Publication Data

US 2002/0120160 A1 Aug. 29, 2002

(30) Foreign Application Priority Data

Dec. 20, 2000 (JP) .................................. 2000-391840

(51) Int. Cl.$^7$ .............................. B01J 31/28; C08F 4/80
(52) U.S. Cl. .................... 502/155; 502/167; 526/172
(58) Field of Search ................. 502/155, 167; 526/172

(56) References Cited

U.S. PATENT DOCUMENTS 6,191,284 B1 * 2/2001 Knochel et al. ............ 548/402

FOREIGN PATENT DOCUMENTS

| EP | 0 893 455 | 1/1999 |
|---|---|---|
| EP | 0 990 664 | 4/2000 |
| JP | 9-27822 | 10/1997 |
| JP | 9-272709 | 10/1997 |
| JP | 9-272713 | 10/1997 |
| JP | 9-278821 | 10/1997 |
| JP | 9-278823 | 10/1997 |
| JP | 2000-143713 | 5/2000 |
| JP | 2000-143715 | 5/2000 |
| JP | 2000-143716 | 5/2000 |
| JP | 2000-143717 | 5/2000 |
| WO | WO 96/23010 | 8/1996 |
| WO | WO 97/02298 | 1/1997 |

OTHER PUBLICATIONS

U.S. Appl. No. 10/094,799, filed Mar. 12, 2002, pending.

U.S. Appl. No. 10/022,772, filed Dec. 20, 2001, pending.

* cited by examiner

*Primary Examiner*—Robert D. Harlan
(74) *Attorney, Agent, or Firm*—Oblon, Spivak, McClelland, Maier & Neustadt, P.C.

(57) ABSTRACT

A transition metal compound having a ligand with an azaferrocene structure or a ferrocene structure. The transition metal compound is used in combination with an activating cocatalyst, as a catalyst for polymerization of olefins.

12 Claims, No Drawings

TRANSITION METAL COMPOUND, COORDINATIVE COMPOUND, CATALYST FOR POLYMERIZATION OF OLEFIN, AND PROCESS FOR POLYMERIZATION OF OLEFIN USING THE CATALYST

BACKGROUND OF THE INVENTION (1) Field of the Invention

This invention relates to a transition metal compound, a coordinative compound, a catalyst for polymerization of an olefin comprising the transition metal compound, and a process for polymerizing an olefin using the catalyst.

(2) Description of the Related Art

It is known that a homogeneous catalyst comprising a combination of a transition metal compound containing a metal of group 4 of the periodic table and having a cyclopentadienyl derivative as a ligand with an aluminoxane exhibits a high activity for polymerization of olefins and is used therefor (for example, Japanese Unexamined Patent Publication [hereinafter abbreviated to "JP-A"] No. S58-19399). Catalysts comprising an organometallic complex having a cyclopentadienyl structure a non-ligand, which include the above-mentioned homogeneous transition metal catalyst, are known as giving a polyolefin having a narrow molecular weight distribution and having a uniform distribution in composition over the polymer.

In recent years, to provide an improved homogeneous catalyst for polymerization of olefins, extensive researches have been made on homogeneous catalysts comprising an organometallic complex having a ligand other than that having a cyclopentadienyl structure, i.e., a ligand containing a heteroatom. For example, as for catalysts for polymerization of olefins comprising an organometallic complex of a transition metal compound with a ligand containing a nitrogen atom, JP-A H8-176217 and JP-A H8-245713 disclose a catalyst for polymerization of an olefin comprising a titanium amide compound containing a titanium metal with a dialkylamine as a ligand. JP-A H10-298216 discloses a catalyst for polymerization of an olefin comprising a transition metal amide compound with a crosslinkable aromatic amine compound as a ligand.

Catalysts for polymerization of olefins comprising an organometallic complex with a ligand comprising a nitrogen atom have also been widely studied from a scientific point of view. Living polymerization of 1-hexene using a catalyst system comprising a diamide complex represented by the formula: $[ArN(CH_2)_3NAr]TiMe_2$, and $B(C_6F_5)_3$ is described in D. H. McConville et al, J. Am. Chem. Soc., vol. 118, p.10008 (1996). Living polymerization of 1-hexene using a catalyst system comprising a diamido complex with a tridentate ligand, represented by the formula: $[(t-BuN-ortho-C_6H_4)_2O]ZrMe_2$ and $B(C_6F_5)_3$, is described in R. R. Schrock et al, J. Am. Chem. Soc., vol. 119, p.3830 (1997). Further, synthesis of a transition metal compound containing a metal of group 4 with a ligand having a bis(borylamide) structure such as $[Mes_2BNCH_2CH_2NBMes_2]^{2-}$ and its catalytic activity for polymerization of ethylene are described in Organometallics, vol. 15, p562 (1996) and Organometallics, vol. 17, p308 (1998).

Recently, it has been reported that a catalyst comprising a bidentate ligand-containing diimine chelate-type nickel complex gives a polyolefin having a structure with many branches introduced therein, which is distinct from a structure of the conventional polyolefins produced by using a metallocene catalyst (for example, WO96/23010). Further, it has been reported that a catalyst comprising an aldimine chelate-type group 4 transition metal complex exhibits greatly enhanced activity for polymerization of an olefin (for example, EP 874,005 (1998), and J. Am. Chem. Soc., vol. 123, p6847 (2001)).

SUMMARY OF THE INVENTION

A primary object of the present invention is to provide a novel transition metal compound having an azaferrocene or ferrocene structure, which is useful as a catalyst for polymerization of olefins.

Another object is to provide a coordinative compound used for production of the above-mentioned novel transition metal compound; and a precursor compound used for production of the coordinative compound.

Still another object is to provide a catalyst for polymerization of an olefin comprising the above-mentioned novel transition metal compound, and a process for polymerizing an olefin using the catalyst, by which polyolefins can be produced with an enhanced efficiency.

In one aspect of the present invention, there is provided a transition metal compound represented by the following formula (1):

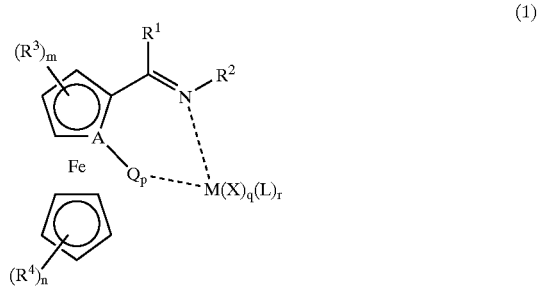

(1)

wherein M represents a transition metal atom selected from the group consisting of metal atoms of group 3 to group 12 of the periodic table.

X represents a hydrogen atom, a halogen atom, a hydrocarbon group having 1 to 20 carbon atoms, a hydrocarbyloxy group having 1 to 20 carbon atoms, an amino group having one or more hydrocarbon groups each with 1 to 20 carbon atoms, a sulfonate group having an organic residue with 1 to 20 carbon atoms, or a non-coordinative anion containing an element selected from the group consisting of B, Al, P and Sb, and, when q is an integer of at least 2, Xs may be the same as or different from each other. A represents a carbon atom, a nitrogen atom or a phosphorus atom.

$R^1$ represents a hydrogen atom, a hydrocarbon group having 1 to 20 carbon atoms, a hydrocarbon group having 1 to 20 carbon atoms and containing at least one halogen atom, or a ferrocenyl group or a substituted ferrocenyl group. $R^2$ represents a hydrogen atom, a hydrocarbon group having 1 to 20 carbon atoms, a hydrocarbon group having 1 to 20 carbon atoms and containing at least one atom selected from halogen, silicon, nitrogen, oxygen and sulfur atoms, or a ferrocenyl group or a substituted ferrocenyl group; and $R^1$ and $R^2$ may form together a ring.

Q represents a hydrogen atom, a hydrocarbon group having 1 to 20 carbon atoms, a silyl group having one or more hydrocarbon groups each with 1 to 20 carbon atoms, an amino group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, a hydrocarbon group having 1 to 20 carbon atoms and containing at least one atom selected from nitrogen, phosphorus, oxygen and sulfur atoms, or oxygen or sulfur; and, when Q contains a coordinative atom, Q can be coordinatively bound to M.

$R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from nitrogen, oxygen, halogen and sulfur atoms, and one of $R^3$s adjacent to Q may form a ring together with Q; and, when m is an integer of at least 2, $R^3$s may be the same as or different from each other, and adjacent $R^3$s may form together a ring. $R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from nitrogen, phosphorus, oxygen, halogen and sulfur atoms; and, when n is an integer of at least 2, $R^4$s may be the same as or different from each other, and adjacent $R^4$s may form together a ring; and $R^3$ and $R^4$ may form together a ring; and, when $R^4$ contains a heteroatom, $R^4$ can coordinate with the transition metal atom M.

L is a coordinate bond-forming compound selected from the group consisting of π electron, ethers, nitriles, amines and phosphines, and L may be bound to X.

m is an integer of 1 to 3, n is an integer of 1 to 5, and p is an integer of 0 or 1. When Q is sulfur or oxygen, the bond between Q and M is a sigma bond. When p is 0 and A is a nitrogen atom or a phosphorus atom, A can be coordinatively bound to M, q is an integer of 1 to 3 and r is an integer of 0 to 3.

In another aspect of the present invention, there is provided a coordinative compound represented by the following formula (5):

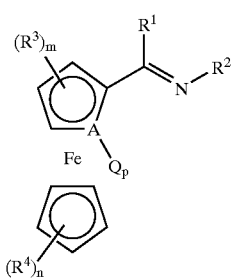

(5)

wherein A represents a carbon atom, a nitrogen atom or a phosphorus atom;

$R^1$ represents a hydrogen atom, a hydrocarbon group having 1 to 20 carbon atoms, a hydrocarbon group having 1 to 20 carbon atoms and containing at least one halogen atom, or a ferrocenyl group or a substituted ferrocenyl group;

$R^2$ represents a hydrogen atom, a hydrocarbon group having 1 to 20 carbon atoms, a hydrocarbon group having 1 to 20 carbon atoms and containing at least one atom selected from halogen, silicon, nitrogen, oxygen and sulfur atoms, or a ferrocenyl group or a substituted ferrocenyl group; and $R^1$ and $R^2$ may form together a ring;

Q represents a hydrogen atom, a hydrocarbon group having 1 to 20 carbon atoms, a silyl group having one or more hydrocarbon groups each with 1 to 20 carbon atoms, an amino group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, a hydrocarbon group having 1 to 20 carbon atoms and containing at least one atom selected from nitrogen, phosphorus, oxygen and sulfur atoms, or a hydroxyl group or a thiol group;

$R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from nitrogen, oxygen, halogen and sulfur atoms, and one of $R^3$s adjacent to Q may form a ring together with Q; and, when m is an integer of at least 2, $R^3$s may be the same as or different from each other, and adjacent $R^3$s may form together a ring;

$R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from the group consisting of nitrogen, phosphorus, oxygen, halogen and sulfur atoms; and, when n is an integer of at least 2, $R^4$s may be the same as or different from each other, and adjacent $R^4$s may form together a ring; and $R^3$ and $R^4$ may form together a ring; and m is an integer of 1 to 3, n is an integer of 1 to 5, and p is an integer of 0 or 1.

In still another aspect of the present invention, there is provided a compound which is a precursor to the coordinative compound represented by formula (5), and which is represented by the following formula (6):

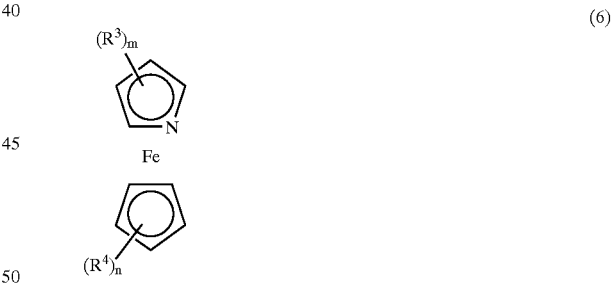

(6)

wherein $R^3$, $R^4$, m and n are the same as defined for formula (5), except that, $R^4$ is not a hydrogen atom, and when n is an integer of 1, $R^4$ is not a methyl group, and, when n is an integer of at least 2, all of the $R^4$s are not simultaneously a methyl group.

In a further aspect of the present invention, there is provided a catalyst for polymerization of an olefin, which comprises the transition metal compound of formula (1).

In a further aspect of the present invention, there is provided a process for polymerizing an olefin in the presence of a catalyst comprising the transition metal compound of formula (1).

DESCRIPTION OF THE PREFERRED EMBODIMENTS

In formula (1) representing the transition metal compound of the present invention, M represents a transition metal atom selected from metals of group 3 to group 12, preferably metals of group 8 to group 12, of the periodic table. More preferably M is selected from Ni, Pd, Fe and Cu.

X represents a hydrogen atom, a halogen atom, a hydrocarbon group having 1 to 20 carbon atoms, a hydrocarbyloxy group having 1 to 20 carbon atoms, an amino group having one or more hydrocarbon groups each with 1 to 20 carbon atoms, a sulfonate group having an organic residue with 1 to 20 carbon atoms, or a non-coordinative anion containing an element selected from B, Al, P and Sb. Preferably, X represents a halogen atom, a hydrocarbon group having 1 to 20 carbon atoms, a sulfonate group having an organic residue with 1 to 20 carbon atoms, or a non-coordinative anion containing an element selected from B, Al, P and Sb. q is an integer of 1 to 3, and, when q is an integer of 2 or 3, Xs may be the same as or different from each other. As specific examples of the halogen atom for X, there can be mentioned chlorine, bromine and iodine atoms. Of these, chlorine and bromine atoms are preferable. The hydrocarbon group having 1 to 20 carbon atoms includes, for example, methyl, ethyl, isopropyl, tert.-butyl, benzyl, allyl, phenyl and o-tolyl groups. The hydrocarbyloxy group having 1 to 20 carbon atoms includes, for example, methoxy, ethoxy, isopropoxy, tert.-butoxy and phenoxy groups. The amino group having one or more hydrocarbon groups each with 1 to 20 carbon atoms includes, for example, dialkylamino groups such as dimethylamino, diethylamino and diisopropylamino groups, diarylamino groups such as a diphenylamino group, and dialkylamino groups such as dibenzylamino groups. The sulfonate group having an organic residue with 1 to 20 carbon atoms includes, for example, trifluoromethanesulfonate and p-toluenesulfonate groups. As specific examples of the non-coordinative anion containing an element selected from B, Al, P and Sb, there can be mentioned tetrakis[3,5-bis(trifluoromethyl)phenyl]borate anion, tetrakis(pentafluorophenyl)borate anion, tetrakis (pentafluorophenyl)aluminite anion, $SbF_6$ anion and $PF_6$ anion.

$R^1$ in formula (1) represents a hydrogen atom, a hydrocarbon group having 1 to 20 carbon atoms, a hydrocarbon group having 1 to 20 carbon atoms and containing at least one halogen atom, or a ferrocenyl group or a substituted ferrocenyl group. Of these, a hydrogen atom and a hydrocarbon group having 1 to 20 carbon atoms are preferable. As specific examples of the hydrocarbon group having 1 to 20 carbon atoms, there can be mentioned methyl, ethyl, propyl, butyl, isopropyl, tert.-butyl, benzyl, phenyl, 2-methylphenyl and naphthyl groups. Of these, methyl and phenyl groups are preferable. As specific examples of the hydrocarbon group having 1 to 20 carbon atoms and containing at least one halogen atom, there can be mentioned trifluoromethyl, trichloromethyl, 2,2,2-trifluoroethyl and difluoromethyl groups. Of these, a trifluoromethyl group is preferable. As specific examples of the substituted ferrocenyl group, there can be mentioned methylferrocenyl, dimethylferrocenyl and tert.-butylferrocenyl groups.

$R^2$ in formula (1) represents a hydrogen atom, a hydrocarbon group having 1 to 20 carbon atoms, a hydrocarbon group having 1 to 20 carbon atoms and containing at least one atom selected from halogen, silicon, nitrogen, oxygen and sulfur atoms, or a ferrocenyl group or a substituted ferrocenyl group. Of these, a hydrocarbon group having 1 to 20 carbon atoms and a hydrocarbon group having 1 to 20 carbon atoms and containing at least one atom selected from halogen, silicon, nitrogen, oxygen and sulfur atoms are preferable. As specific examples of the hydrocarbon group having 1 to 20 carbon atoms in $R^2$, there can be mentioned methyl, ethyl, propyl, isopropyl, tert.-butyl, benzyl, phenyl, 2-methylphenyl, 2,6-dimethylphenyl, 2-isopropylphenyl, 2,6-diisopropylphenyl, 2-tert.butylphenyl, mesityl, 2-biphenyl, naphthyl and adamantyl groups. Of these, 2-methylphenyl, 2-isopropylphenyl, 2-tert.butylphenyl and 2-biphenyl groups are preferable. As specific examples of the hydrocarbon group having 1 to 20 carbon atoms and containing at least one atom selected from halogen, silicon, nitrogen, oxygen and sulfur atoms, there can be mentioned 2-(trifluoromethyl)phenyl, 2-(trichloromethyl)phenyl, 2-methyl-4-chlorophenyl, 2-(trimethylsilyl)phenyl, 2,6-di(trimethylsilyl)phenyl, 2-(dimethylaminomethyl)phenyl, 2-(dimethylaminomethyl)phenyl, 2-(methoxymethyl)phenyl, 2-(phenoxymethyl)phenyl, 2-(methylthiomethyl)phenyl, 2-(phenylthiomethyl)phenyl, 2-pyridyl, 2-quinolyl, 2-(3-benzyloxypyridyl), 5-(1,3-dimethylpyrazolyl), 2-(methylthio)-5-(trifluoromethyl)phenyl and 2-(1H-pyrrol-1-yl)phenyl groups. Of these, (trifluoromethyl)phenyl, 2-(trichloromethyl)phenyl, 2-methyl-4-chlorophenyl, 2-(trimethylsilyl)phenyl, 2-(diphenylaminomethyl)phenyl and 2-(methoxymethyl)phenyl groups are preferable. As specific examples of the substituted ferrocenyl group, there can be mentioned a methylferrocenyl group, a dimethylferrocenyl group, a tert.-butylferrocenyl group and a ferrocenyl group having a tetramethylcyclopentadienyl (hereinafter abbreviated to Cp* when appropriate) group. $R^1$ and $R^2$ in formula (1) may form together a ring.

Q in formula (1) represents a hydrogen atom, a hydrocarbon group having 1 to 20 carbon atoms, a silyl group having one or more hydrocarbon groups each with 1 to 20 carbon atoms, an amino group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, a hydrocarbon group having 1 to 20 carbon atoms and containing at least one atom selected from nitrogen, phosphorus oxygen and sulfur atoms, or oxygen or sulfur. Of these, an amino group having one or more hydrocarbon groups each with 1 to 20 carbon atoms and a hydrocarbon group having 1 to 20 carbon atoms and containing at least one nitrogen atom are preferable. When Q contains a coordinative atom, Q can be coordinatively bound to M. As specific examples of the hydrocarbon group having 1 to 20 carbon atoms in Q, there can be mentioned methyl, ethyl, tert.-butyl and phenyl group. As specific examples of the silyl group having one or more hydrocarbon groups each with 1 to 20 carbon atoms, there can be mentioned trimethylsilyl, tert.-butyldimethylsilyl and triphenylsilyl groups. As specific examples of the amino group having one or more hydrocarbon groups each with 1 to 20 carbon atoms, there can be mentioned dimethylamino, diethylamino, diphenylamino, or a pyridyl group bound to the adjacent $R^3$ group or a substituted pyridyl group bound to the adjacent $R^3$ group. Of these, a pyridyl group bound to the adjacent $R^3$ group and a substituted pyridyl group bound to the adjacent $R^3$ group are preferable. As specific examples of the phosphino group having one or more hydrocarbon groups each with 1 to 20 carbon atoms, there can be mentioned dimethylphosphino, dicyclohexylphosphino, di-tert.-butylphosphino and diphenylphosphino, and azaphosphines such as bis(diisopropylamino) phosphino, bis(pyrrolidinyl) phosphino, 1-(N,N-dimethyl-2,5-diaza-1-phosphinocyclopentyl) and 1-(N,N-diphenyl-2,5-diaza-1-phosphinocyclopentyl) groups, As specific examples of the oxy group having a hydrocarbon group with 1 to 20 carbon atoms, there can be mentioned methyloxy, phenoxy, 2-methylphenoxy and benzyloxy groups. As specific examples of the group having a hydrocarbon group with 1 to 20 carbon atoms, there can be mentioned methylthio, phenylthio and 2-methylphenylthio groups. As specific examples of the hydrocarbon group having 1 to 20 carbon atoms and containing at least one atom selected from nitrogen, phosphorus, oxygen and sulfur atoms, there can be mentioned N-phenyliminomethyl, N-(2-tolyl)iminomethyl, dimethylaminomethyl, diphenylaminomethyl, phenylaminomethyl, diphenylphosphinomethyl, dicyclohexylphosphinomethyl. di(tert.-butylphosphino)methyl, methoxymethyl, (1-methoxymethyl)ethyl, phenoxymethyl, (2-methylphenoxy)methyl, methylthiomethyl and phenylthiomethyl groups. Of these, N-phenyliminomethyl and N-(2-tolyl)iminomethyl groups are preferable. When Q is oxygen or sulfur, Q can be sigma-bound to a transition metal M. p is an integer of 0 or 1, preferably 0.

$R^3$ in formula (1) represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from nitrogen, oxygen, halogen and sulfur atoms. Preferably, $R^3$ represents a hydrogen atom, a hydrocarbon group having 1 to 20 carbon atoms, or a hydrocarbon group having 1 to 20 carbon atoms and containing an oxygen atom. As specific examples of the hydrocarbon having 1 to 20 carbon atoms, there can be mentioned methyl, ethyl, butyl, isopropyl, tert.-butyl, phenyl, 2-methylphenyl and 4-methoxyphenyl. As specific examples of the silyl group having one or more hydrocarbon groups each with 1 to 20 carbon atoms, there can be mentioned trimethylsilyl, tert.-butyldimethylsilyl and triphenylsilyl groups. As specific examples of the hydrocarbon having 1 to 20 carbon atoms and containing a nitrogen, oxygen, halogen or sulfur atom, there can be mentioned chloromethyl, methoxymethyl, dimethylaminomethyl, formyl, N-(2-methylphenyl)iminomethyl, N-(2-isopropylphenyl)iminomethyl, methylthiomethyl and phenylthiomethyl groups. Q and one of adjacent $R^3$ may bond to each other to form a ring. Such a ring includes, for example, a pyridine ring, m is an integer of 1 to 3, and, when m is 2 or 3, two or three $R^3$s may be either the same as or different from each other, and adjacent $R^3$s may bond to each other to form a ring.

n of $(R^4)_n$ in formula (1) is an integer of 1 to 5, and, when n is at least 2. $R^4$s may be the same as or different from each other. $R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from nitrogen, phosphorus, oxygen, halogen and sulfur atoms. Of these, a hydrogen atom, a hydrocarbon group having 1 to 20 carbon atoms, a silyl group having one or more hydrocarbon groups each with 1 to 20 carbon atoms, and a hydrocarbon group having 1 to 20 carbon atoms and containing at least one atom selected from nitrogen, oxygen and halogen atoms are preferable. As specific examples of the hydrocarbon group having 1 to 20 carbon atoms in $R^4$, there can be mentioned methyl, ethyl, butyl, isopropyl, tert.-butyl, phenyl, 2-methylphenyl and 4-tert.-butylphenyl groups. As specific examples of the silyl group having one or more hydrocarbon groups each with 1 to 20 carbon atoms, there can be mentioned trimethylsilyl, tert.-butyldimethylsilyl and triphenylsilyl groups. As specific examples of the phosphino group having one or more hydrocarbon groups each with 1 to 20 carbon atoms, there can be mentioned dimethylphosphino, dicyclohexylphosphino, di-(tert.-butyl)phosphino and diphenylphosphino groups. As specific examples of the oxy group having a hydrocarbon group with 1 to 20 carbon atoms, there can be mentioned methyloxy, phenoxy, 2-methylphenoxy and benzyloxy groups. As specific examples of the thio group having a hydrocarbon group with 1 to 20 carbon atoms, there can be mentioned methylthio, phenylthio and 2-methylphenylthio groups. As specific examples of the hydrocarbon group having 1 to 20 carbon atoms and containing at least one atom selected from nitrogen, phosphorus, oxygen, halogen and sulfur atoms, there can be mentioned N-(tert.-butyl)iminomethyl, N-phenyliminomethyl, N-(2-tolyl)iminomethyl, 3-(dimethylaminomethyl)phenyl, dimethylaminomethyl, 1-(dimethylamino)ethyl, diphenylaminomethyl, phenylmethylaminomethyl, diphenylphosphinomethyl, dicyclohexylphosphinomethyl, di(tert.-butylphosphino) methyl, 4-methoxyphenyl, 3-(methoxymethyl)phenyl, methoxymethyl, 1-(methoxymethyl)ethyl, phenoxymethyl, (2-methylphenoxy)methyl, 4-fluorophenyl, 3-trifluoromethyl) phenyl, 2,2,2-trifluorethyl, methylthiomethyl and phenylthiomethyl groups.

When $R^4$ contains a heteroatom, $R^4$ can coordinate with the transition metal atom M.

L in formula (1) is a coordinate bond-forming compound selected from π electron, others, nitriles, amines and phosphines. As specific examples of L, there can be mentioned ethylene, propylene, styrene, dimethyl ether, diethyl ether, dibutyl ether, acetonitrile, benzonitrile, trimethylamine, triethylamine, N,N-dimethylaniline, N-methyldiphenylamine, triphenylphosphine and tricyclohexylphosphine. r is an integer of 0 to 3.

X and L in formula (1) may be bound together to form a group such as, for example, π-allyl, 1-methyl-π-allyl, 2-methyl-π-allyl and 1-phenyl-π-allyl groups.

The transition metal compound of the present invention having a ligand with an azaferrocene structure or a ferrocene structure, represented by formula (1), preferably includes those which are represented by the following formulae (2), (3) and (4).

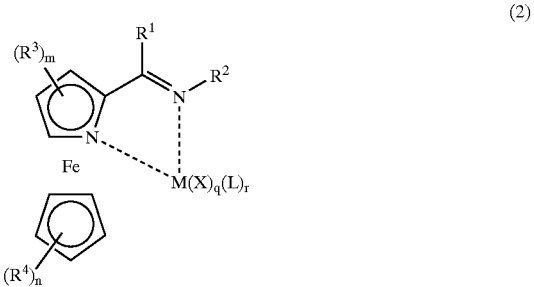

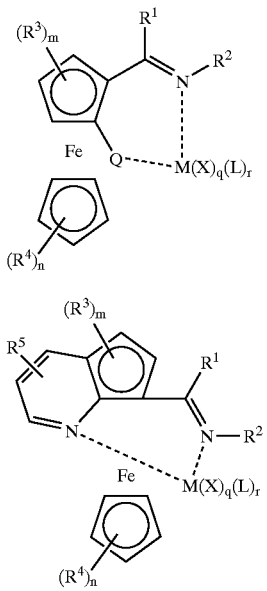

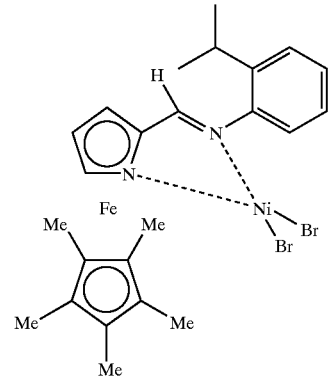

In formula (4), $R^5$ represents a hydrogen atom, a hydrocarbon group having 1 to 20 carbon atoms, or an amino group having one or more hydrocarbon groups each with 1 to 20 carbon atoms. As specific examples of the hydrocarbon group having 1 to 20 carbon atoms, there can be mentioned methyl, ethyl, butyl, isopropyl, tert.-butyl, phenyl and 2-methylphenyl groups. As specific examples of the amino group having one or more hydrocarbon groups each with 1 to 20 carbon atoms, there can be mentioned dimethylamino, diethylamino, N-piperazinyl, N-piperidinyl, N-pyrrolidinyl and diphenylamino groups. m in formula (4) is an integer of 1 or 2.

As specific examples of the transition metal compound of the present invention having a ligand with an azaferrocene structure or a ferrocene structure, there can be mentioned the transition metal complexes represented by the following formulae, which by no means limit the transition metal compound of the present invention. In the transition metal compound having a ligand with an azaferrocene structure or a ferrocene structure of the present invention, when the azaferrocene ring or ferrocene ring has a planar asymmetry, or when $R^2$ has an asymmetrical carbon atom, a racemic modification or an optically active substance may be used.

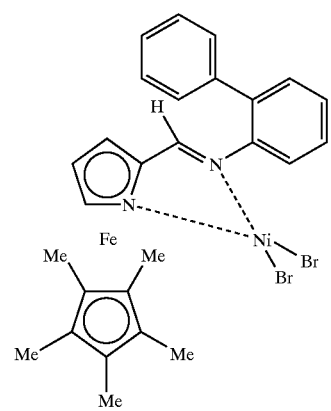

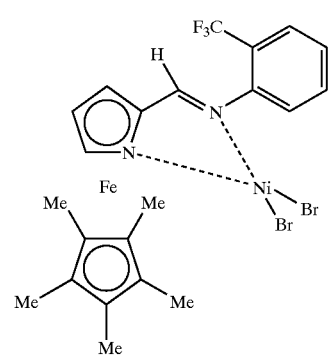

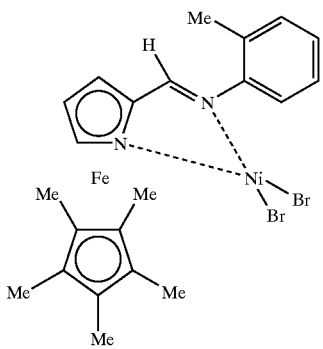

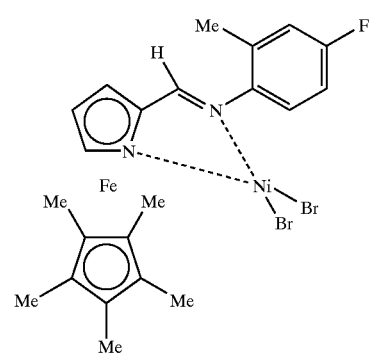

-continued
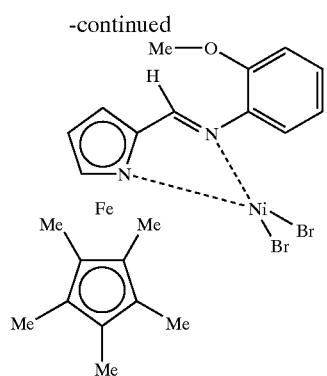
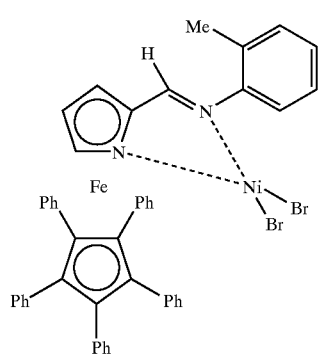
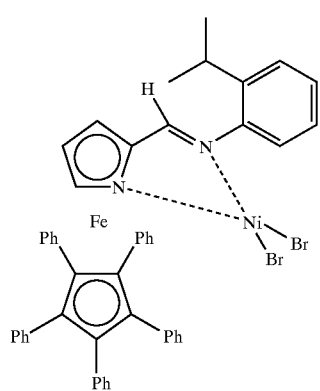
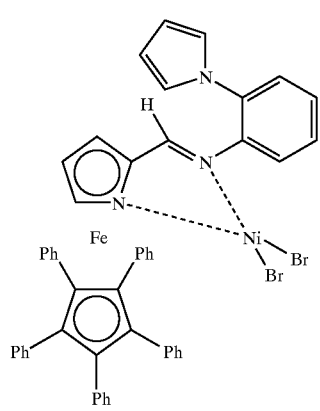
-continued
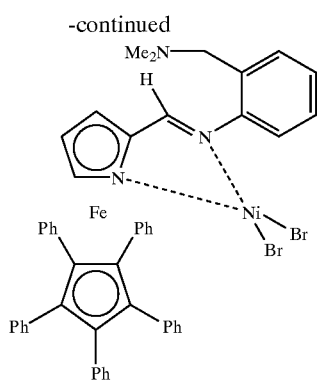
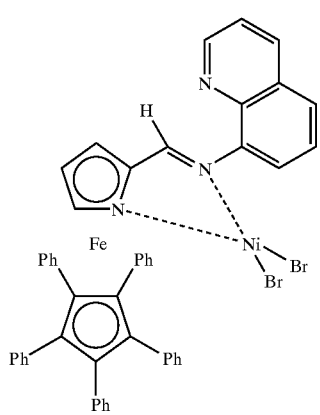
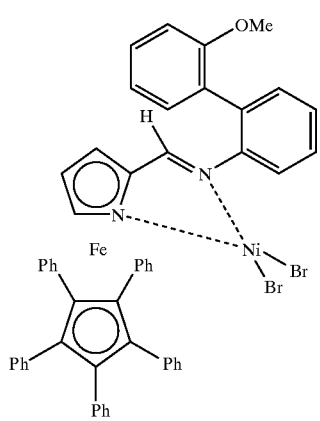
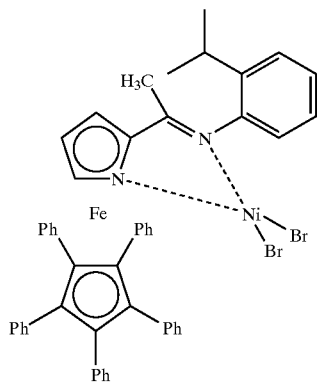

-continued
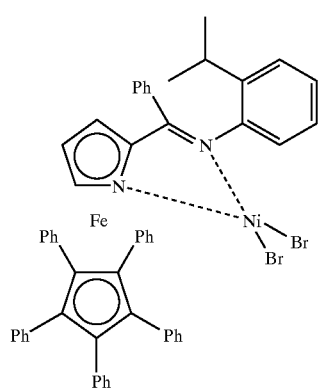
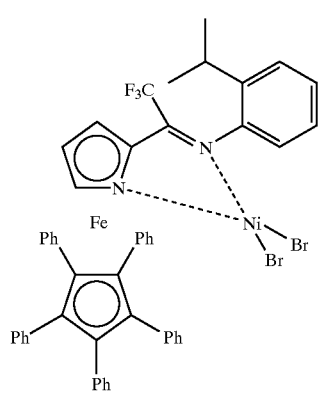
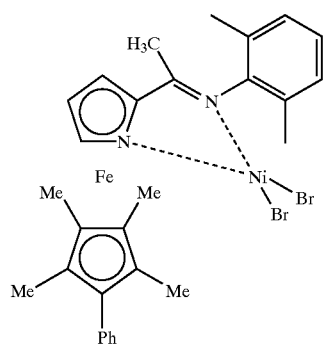
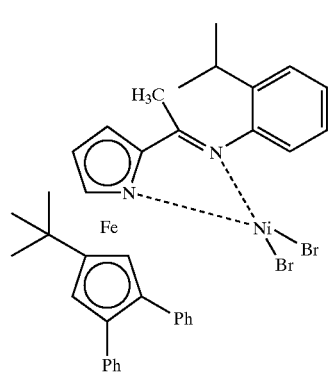
-continued
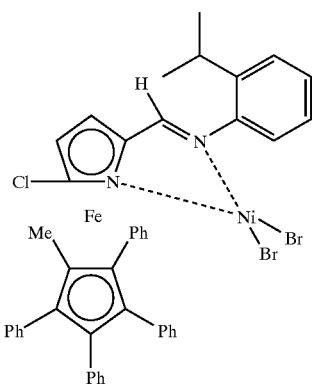
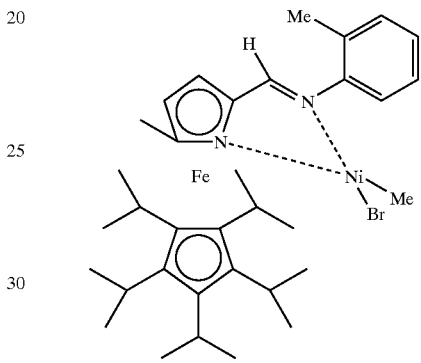
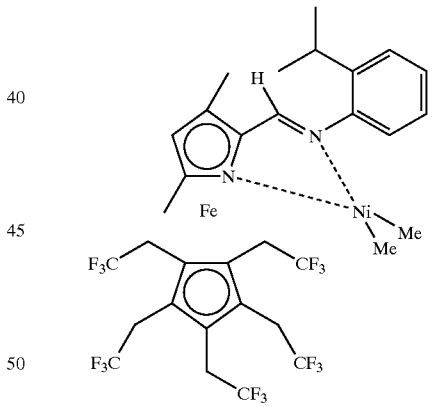
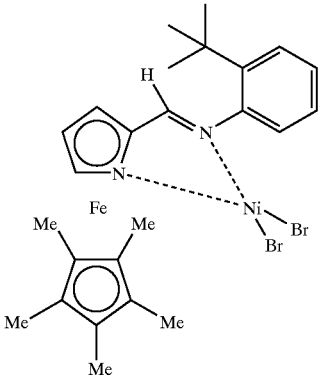

-continued
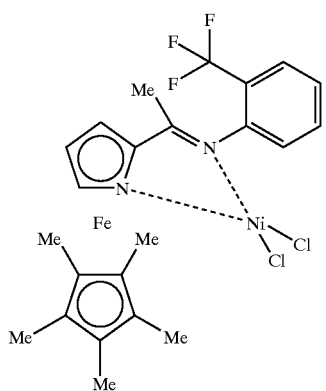
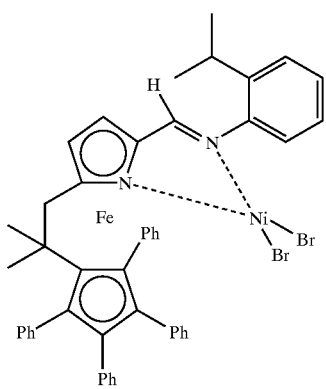
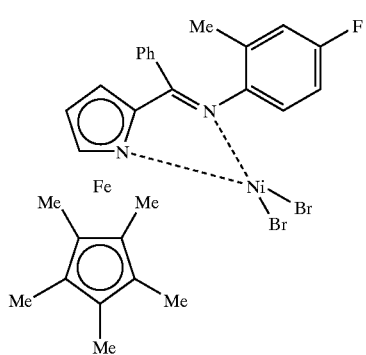
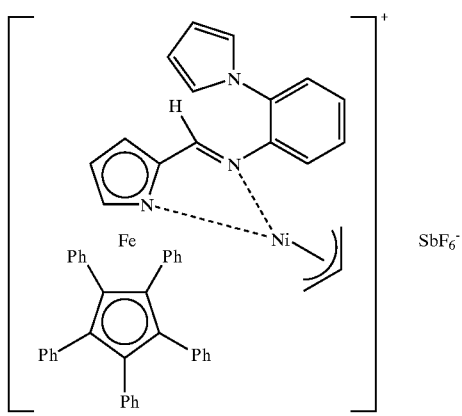
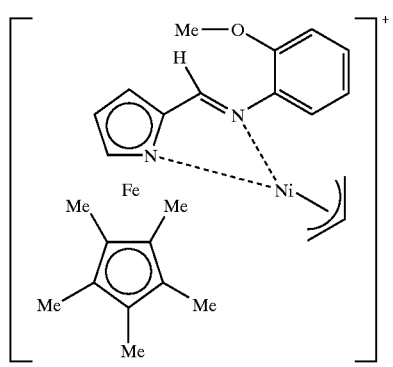
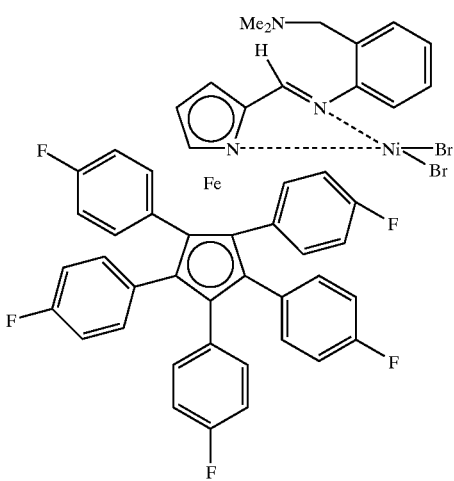

-continued
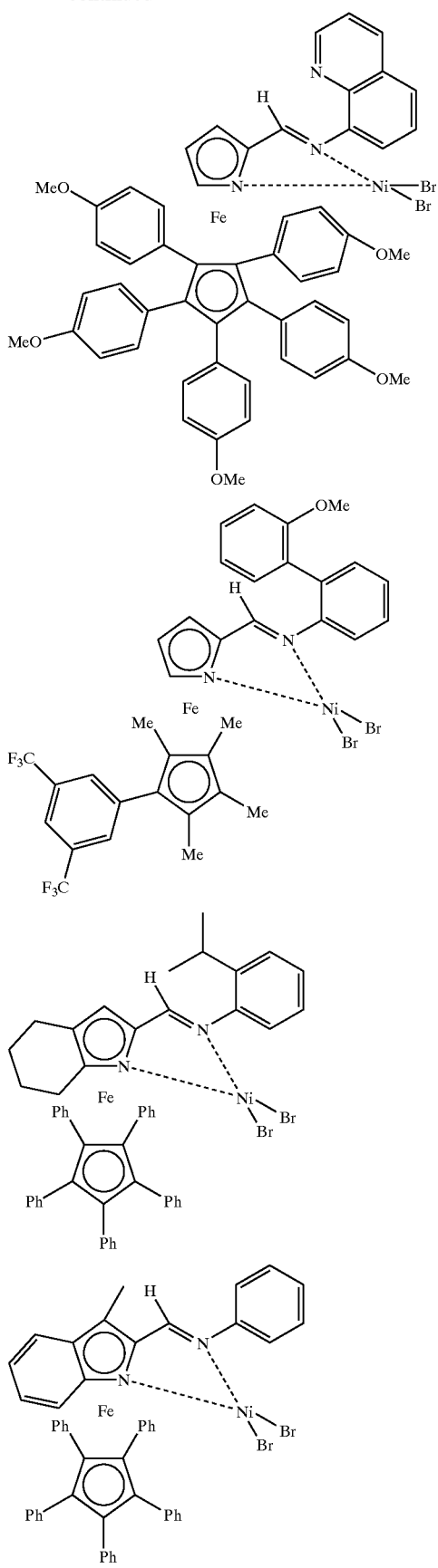
-continued
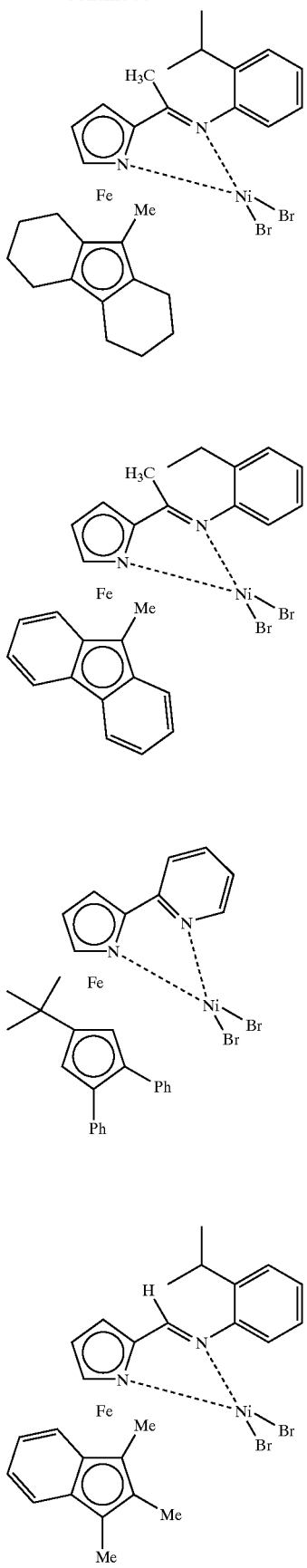

-continued
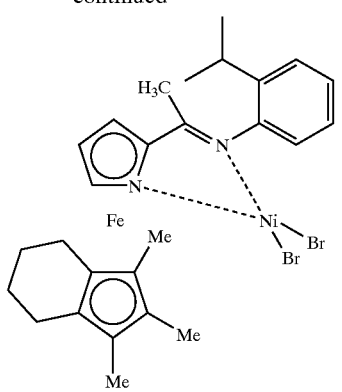
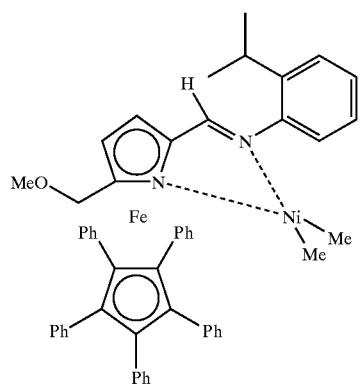
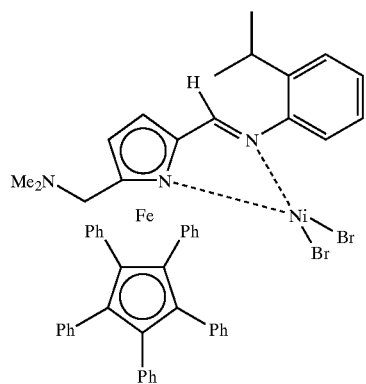
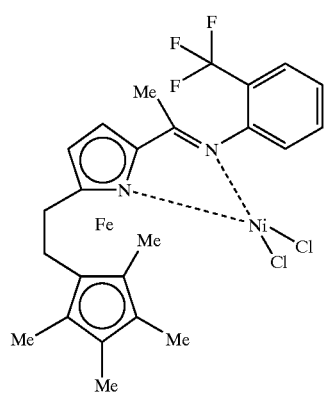
-continued
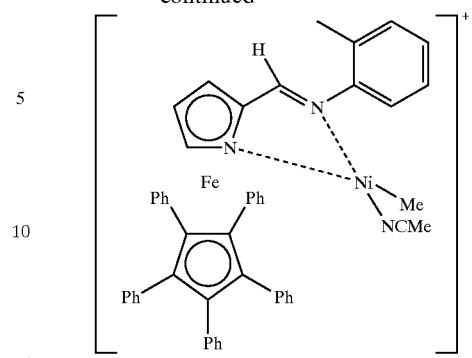
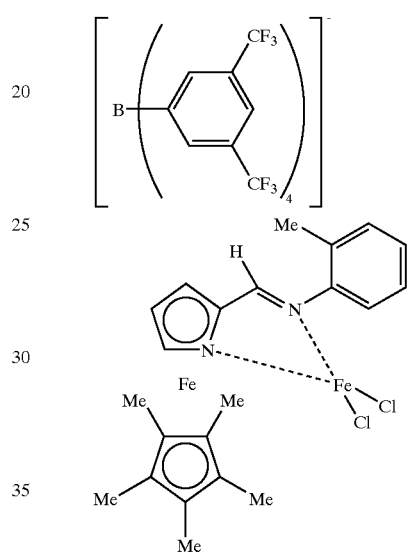
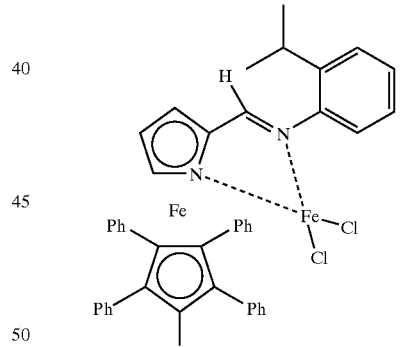
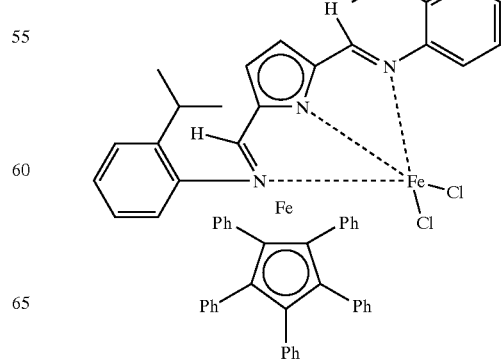

-continued
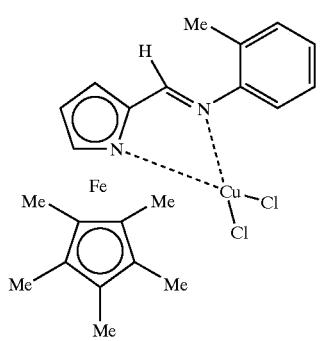
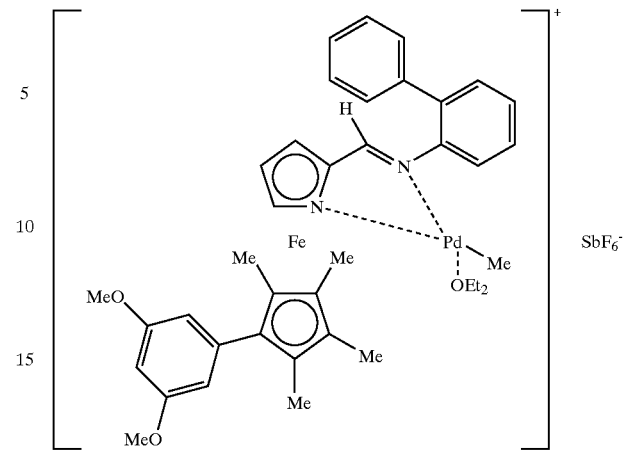
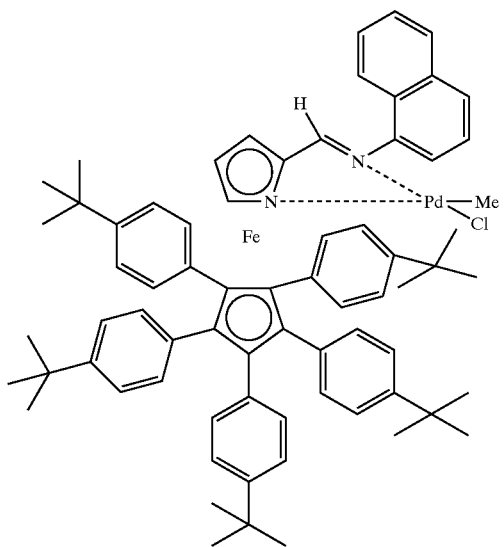
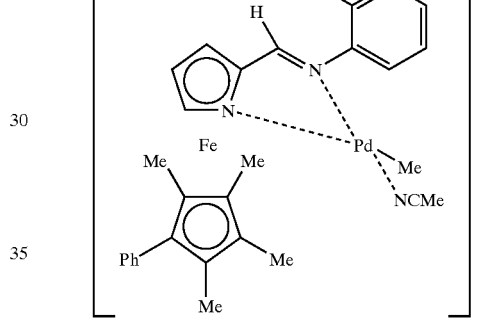
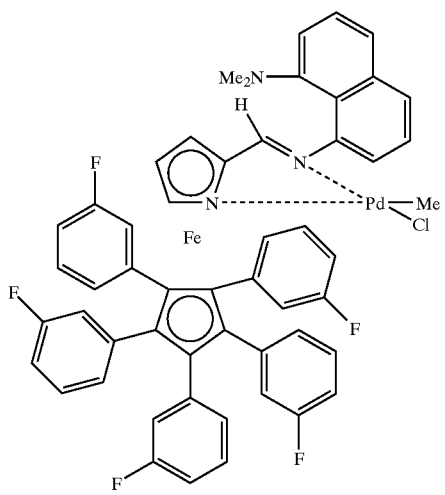
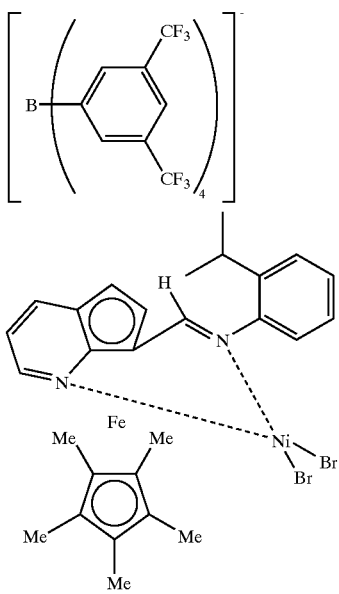

-continued
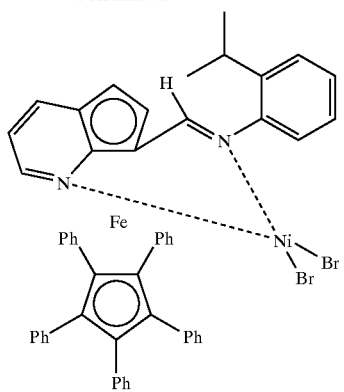
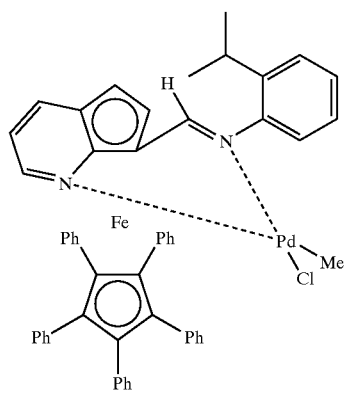
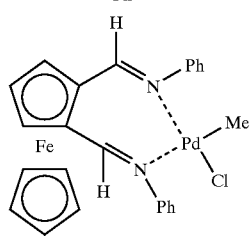
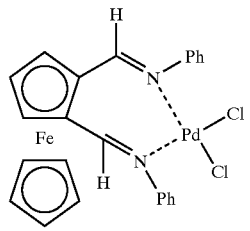
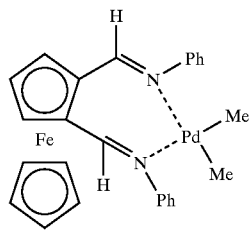
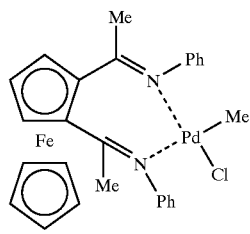
-continued
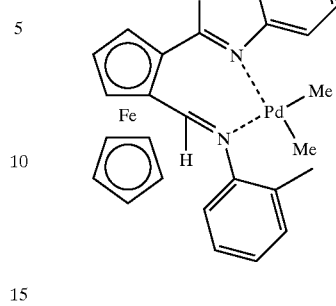
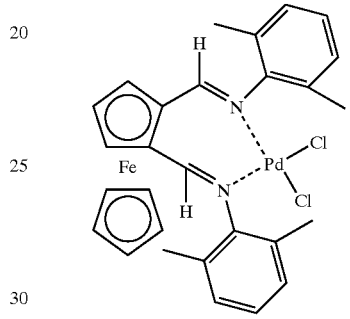
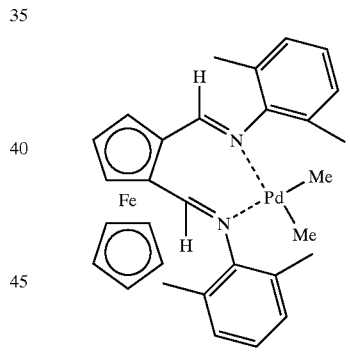
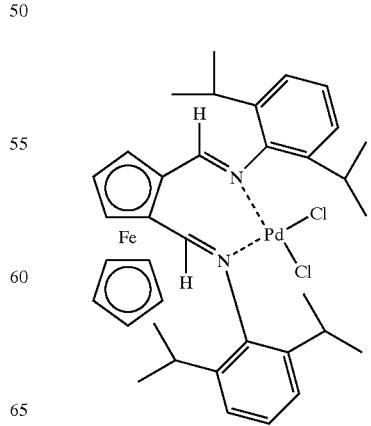

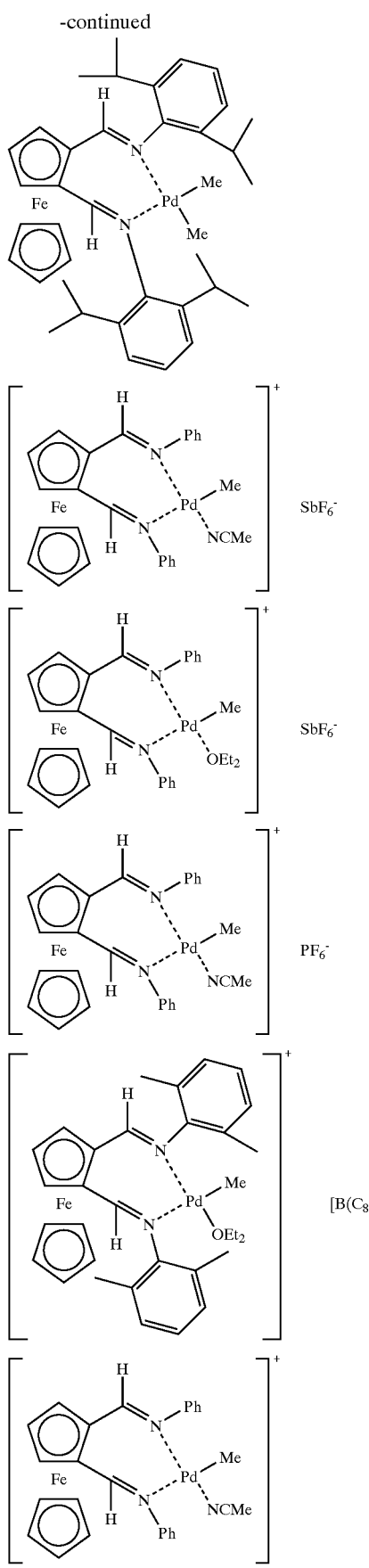
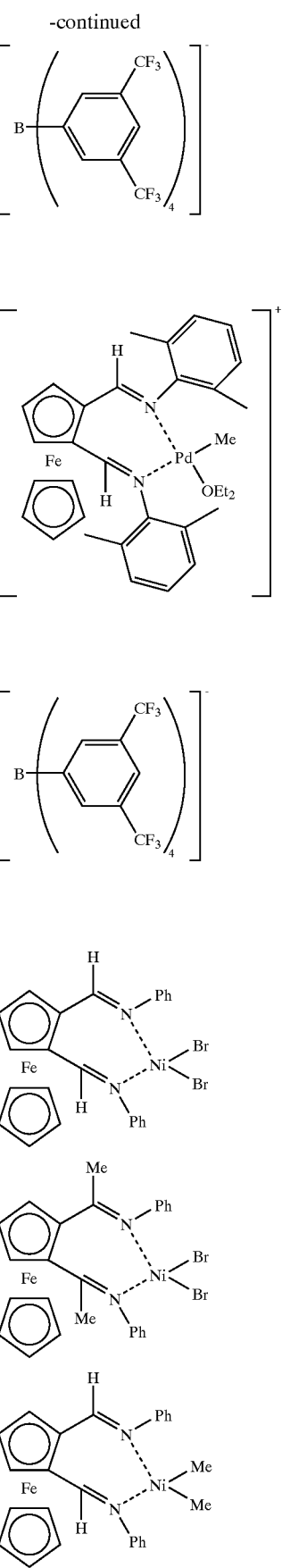

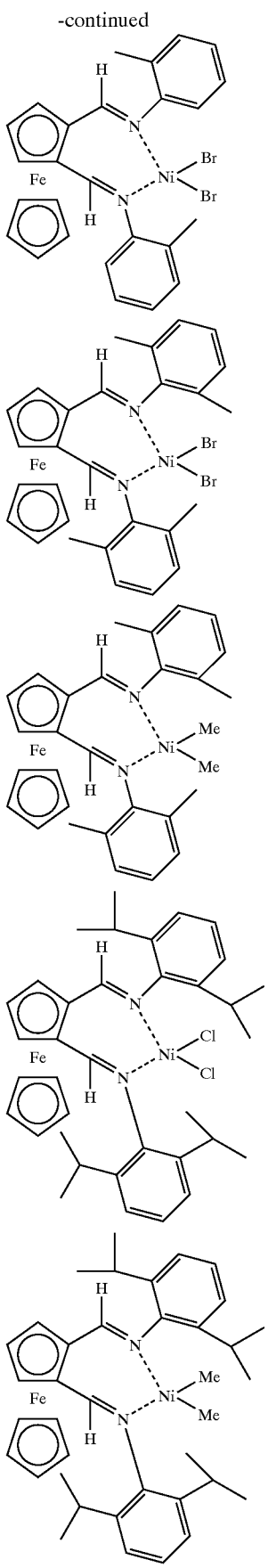
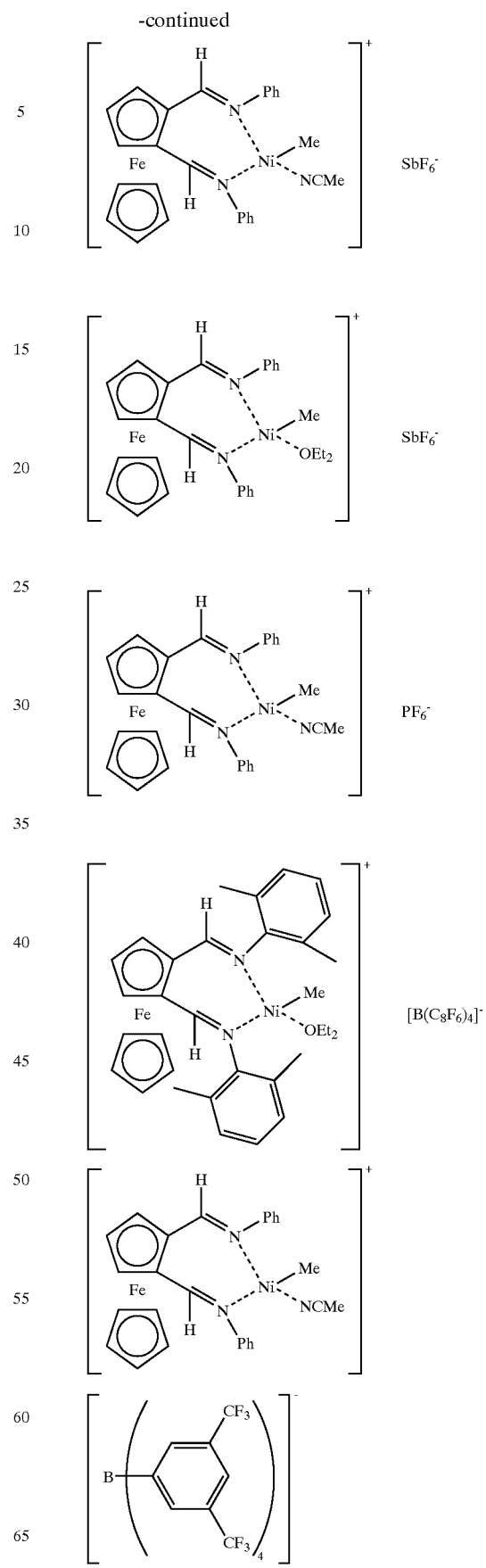

-continued
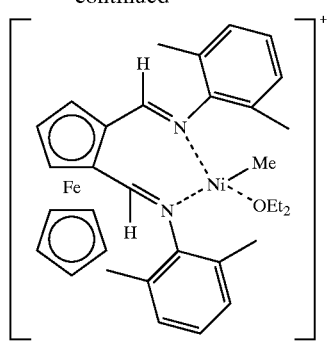
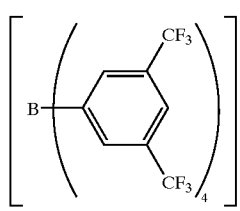
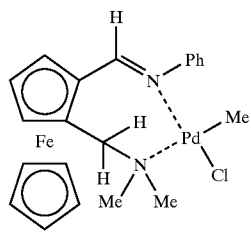
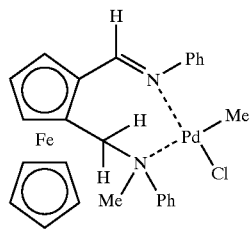
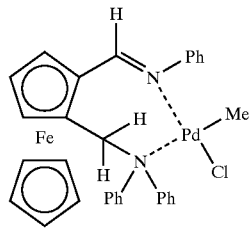
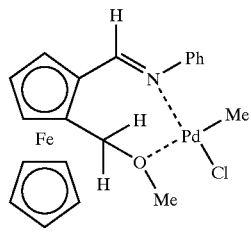
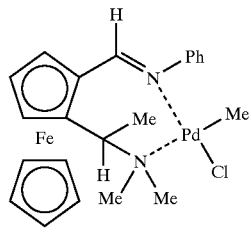
-continued
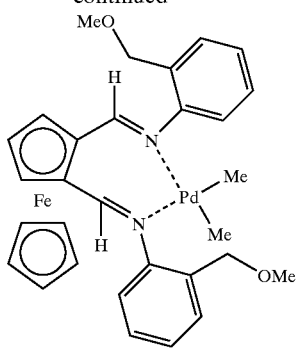
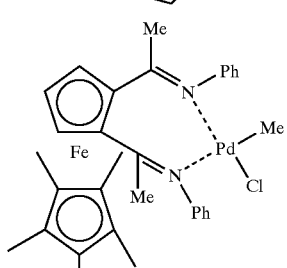
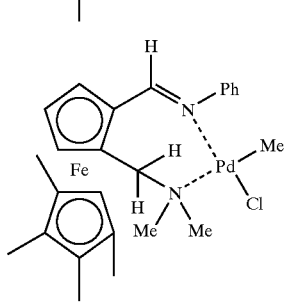
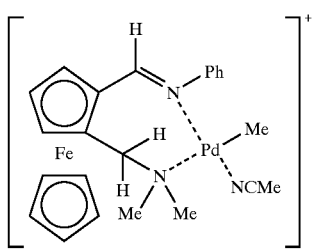
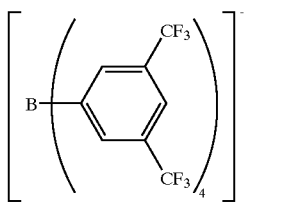
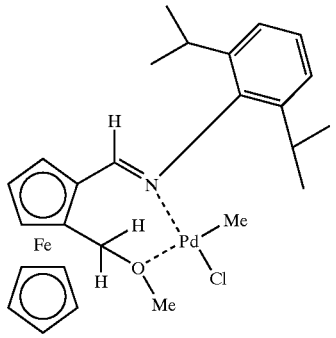

-continued
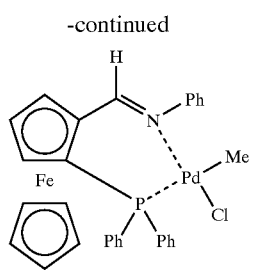
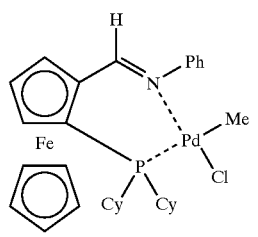
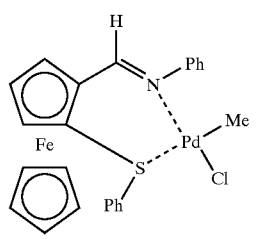
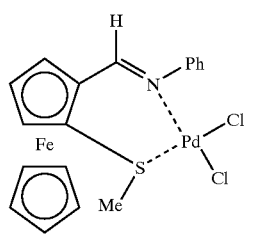
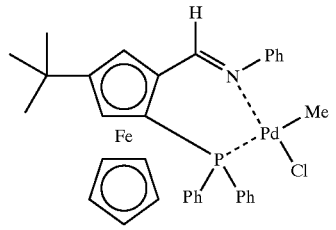
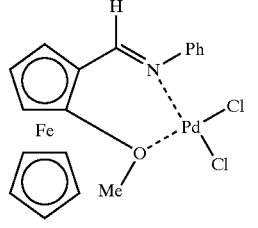
-continued
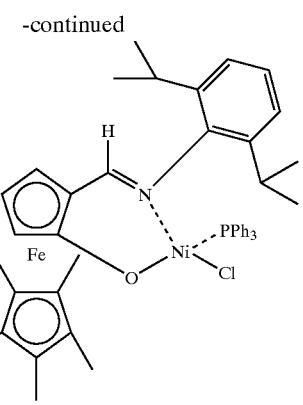
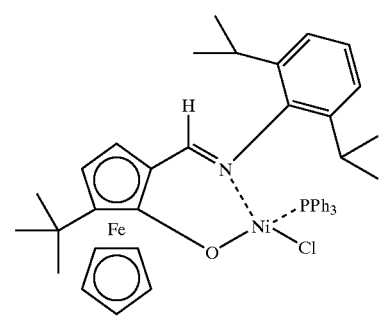
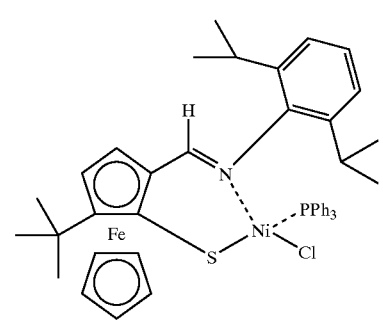
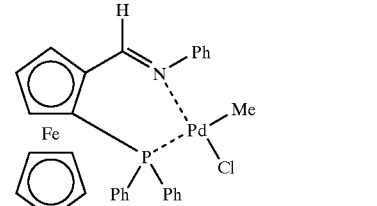
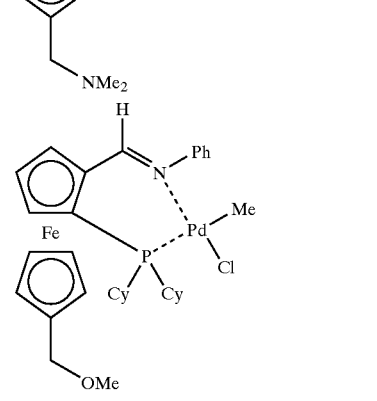

-continued
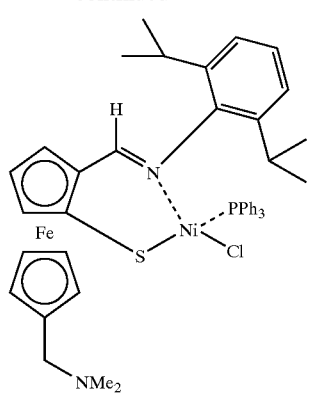
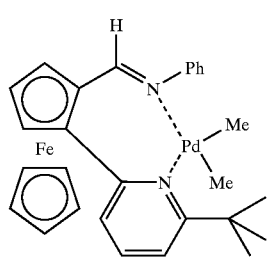
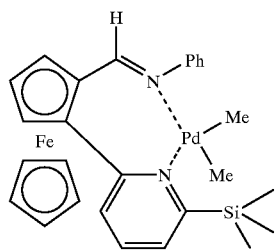
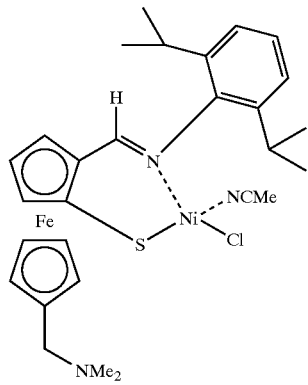
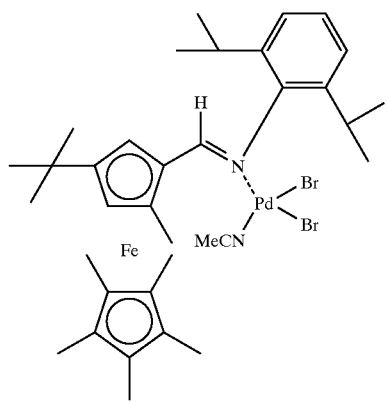
-continued
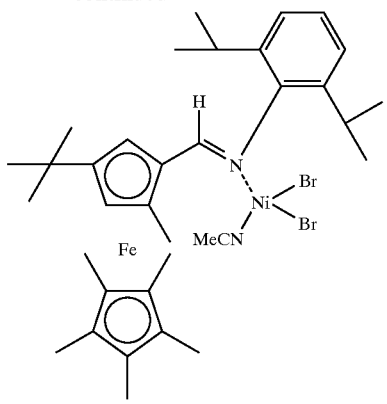
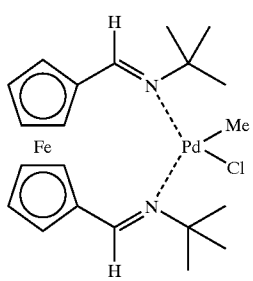
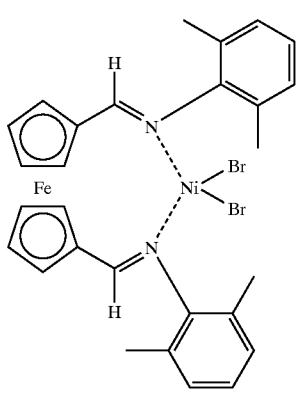
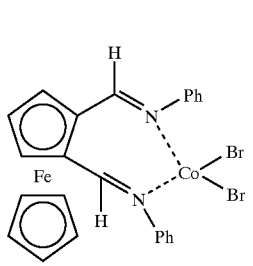
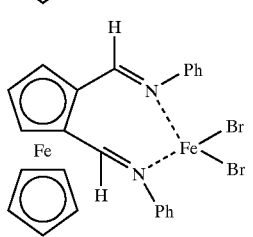

-continued
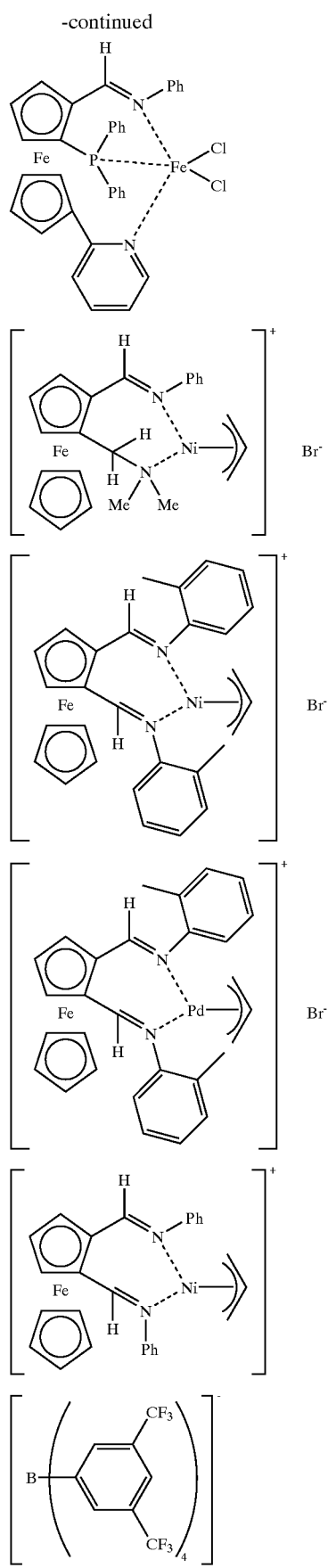
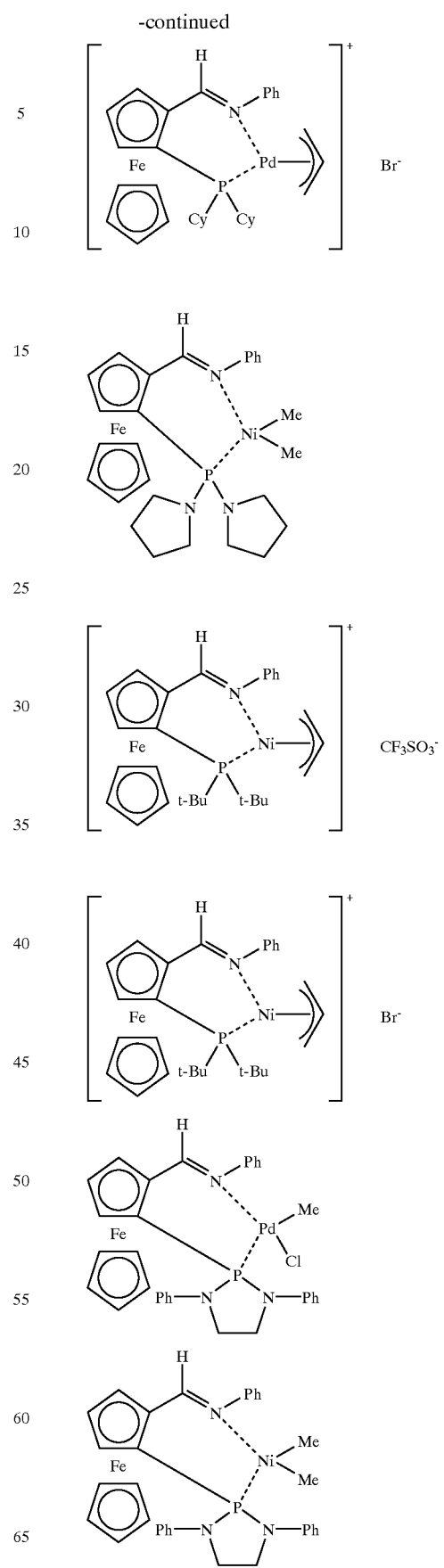

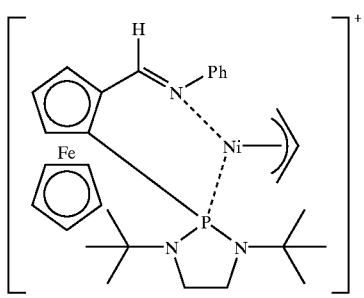

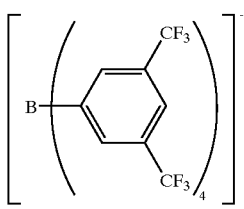

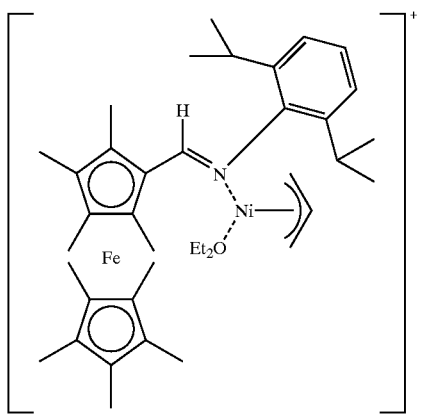

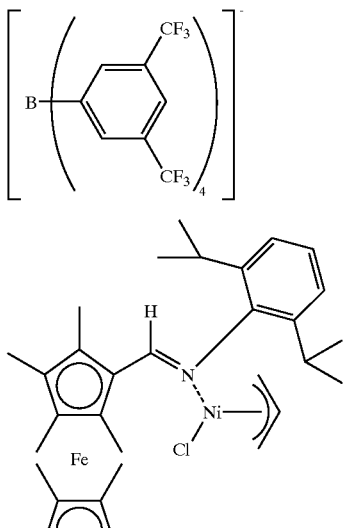

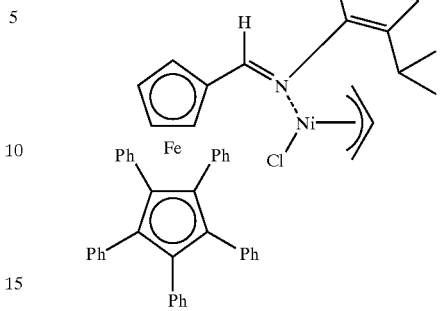

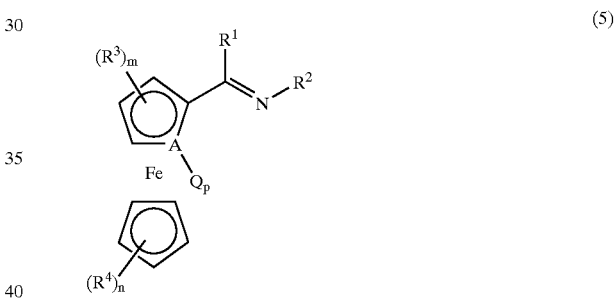

The transition metal compound of the present invention having a ligand with an azaferrocene structure or a ferrocene structure, represented by formula (1), can be synthesized by a process wherein a corresponding coordinative compound having a azaferrocene structure or a ferrocene structure is synthesized and then the coordinative compound is made into a complex. The corresponding coordinative compound having a azaferrocene structure or a ferrocene structure is represented by the following formula (5).

$$\text{(5)}$$

wherein A represents a carbon atom, a nitrogen atom or a phosphorus atom;

$R^1$ represents a hydrogen atom, a hydrocarbon group having 1 to 20 carbon atoms, a hydrocarbon group having 1 to 20 carbon atoms and containing at least one halogen atom, a ferrocenyl group or a substituted ferrocenyl group;

$R^2$ represents a hydrogen atom, a hydrocarbon group having 1 to 20 carbon atoms, a hydrocarbon group having 1 to 20 carbon atoms and containing at least one atom selected from halogen, silicon, nitrogen, oxygen and sulfur atoms, a ferrocenyl group, or a substituted ferrocenyl group: and $R^1$ and $R^2$ may form together a ring;

Q represents a hydrogen atom, a hydrocarbon group having 1 to 20 carbon atoms, a silyl group having one or more hydrocarbon groups each with 1 to 20 carbon atoms, an amino group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, a hydrocarbon group having 1 to 20 carbon atoms and containing at least one atom selected from nitrogen, phosphorus, oxygen and sulfur atoms, or a hydroxyl group or a thiol group;

$R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from nitrogen, oxygen, halogen and sulfur atoms, and one of $R^3$s adjacent to Q may form a ring together with Q; and, when m is an integer of at least 2, $R^3$s may be the same as or different from each other, and $R^3$s may form together a ring;

$R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from nitrogen, phosphorus, oxygen, halogen and sulfur atoms; and, when n is an integer of at least 2, $R^4$s may be the same as or different from each other, and adjacent $R^4$s may form together a ring; and $R^3$ and $R^4$ may form together a ring; and m is an integer of 1 to 3, n is an integer of 1 to 5, and p is an integer of 0 or 1.

Substituents $R^1$ through $R^4$ in the coordinative compound of formula (5) are the same as substituents $R^1$ through $R^4$, respectively, in the transition metal compounds of formulae (1), (2) and (3).

As specific examples of the coordinative compound of formula (5) of the present invention, there can be mentioned compounds represented by the following formulae.

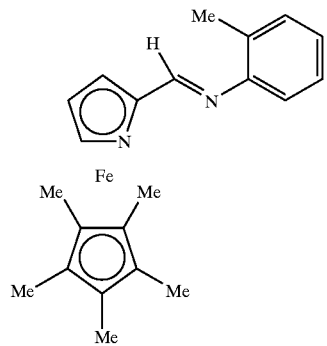

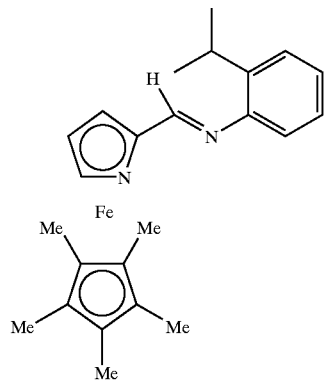

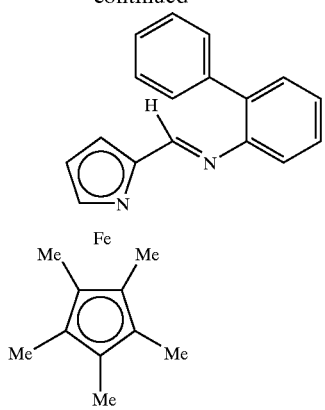

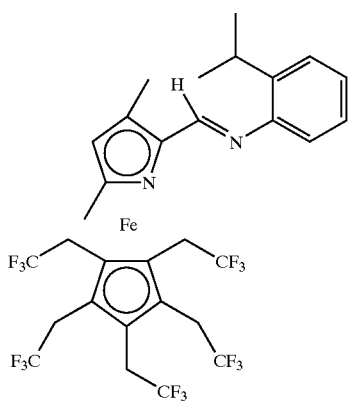

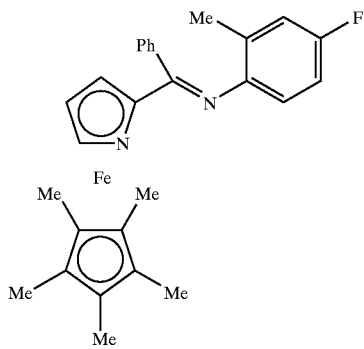

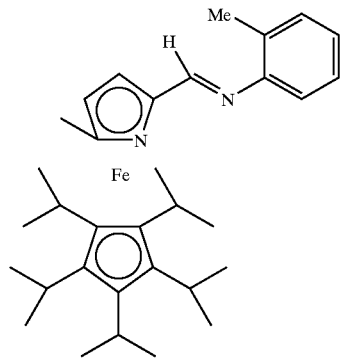

-continued
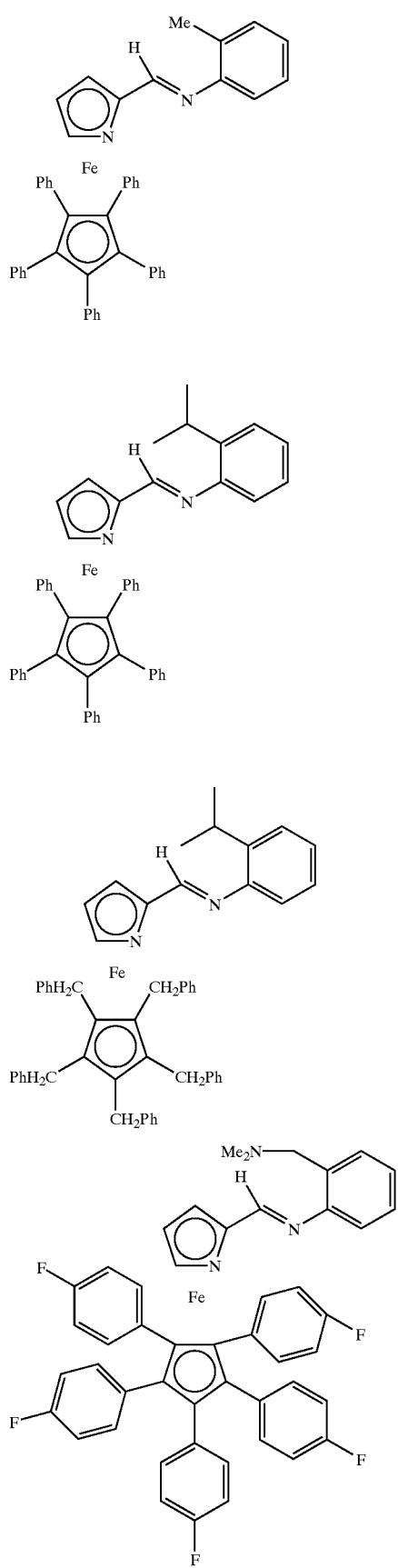
-continued
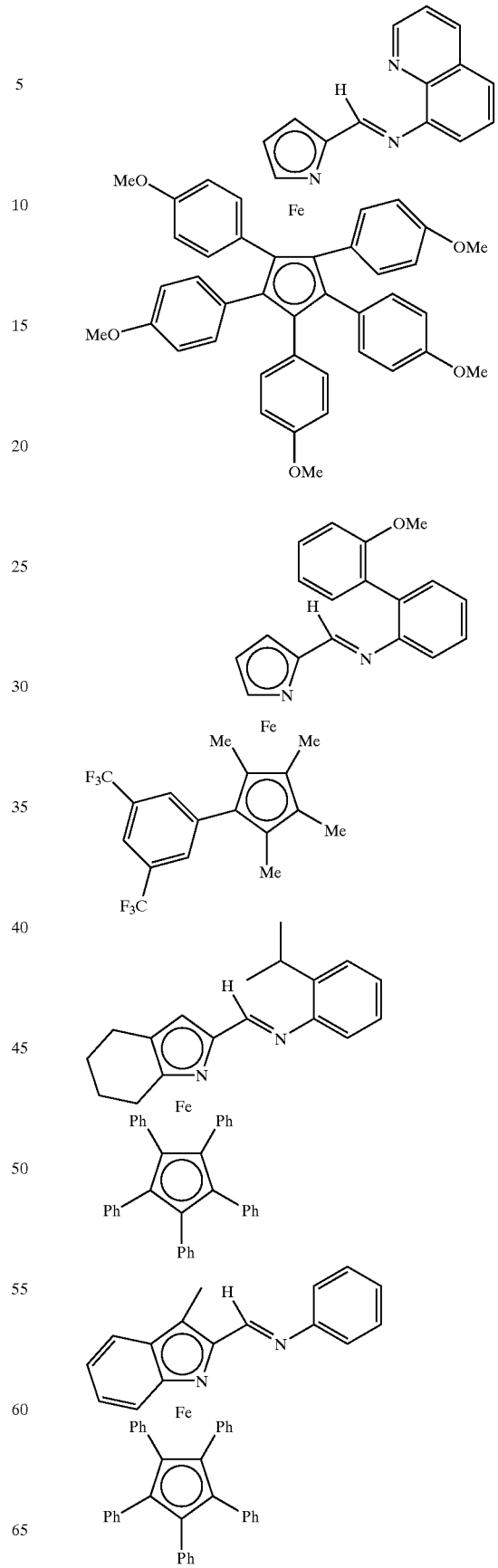

-continued
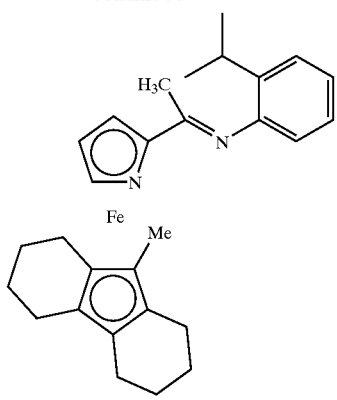
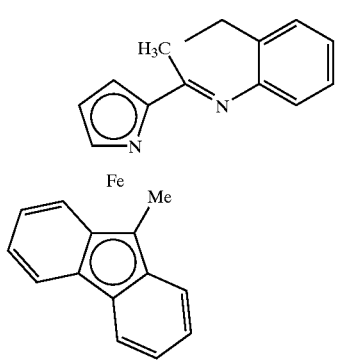
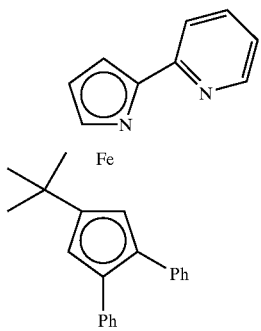
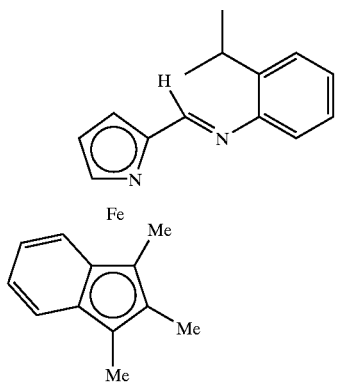
-continued
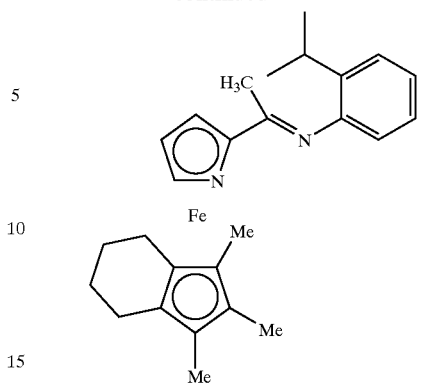
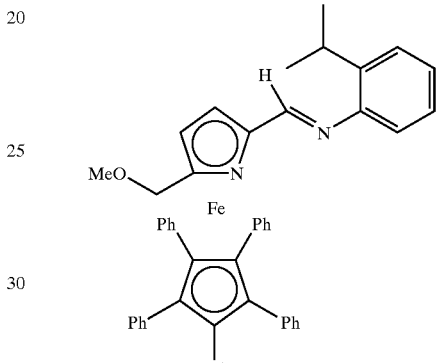
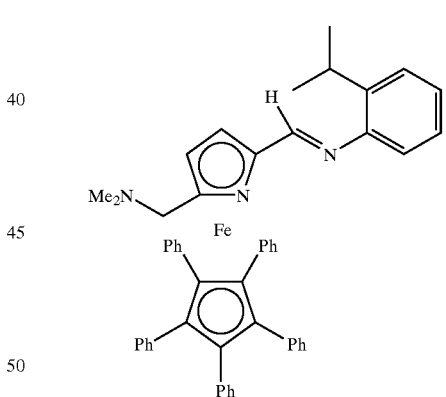
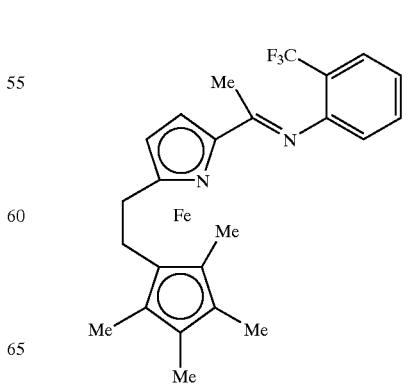

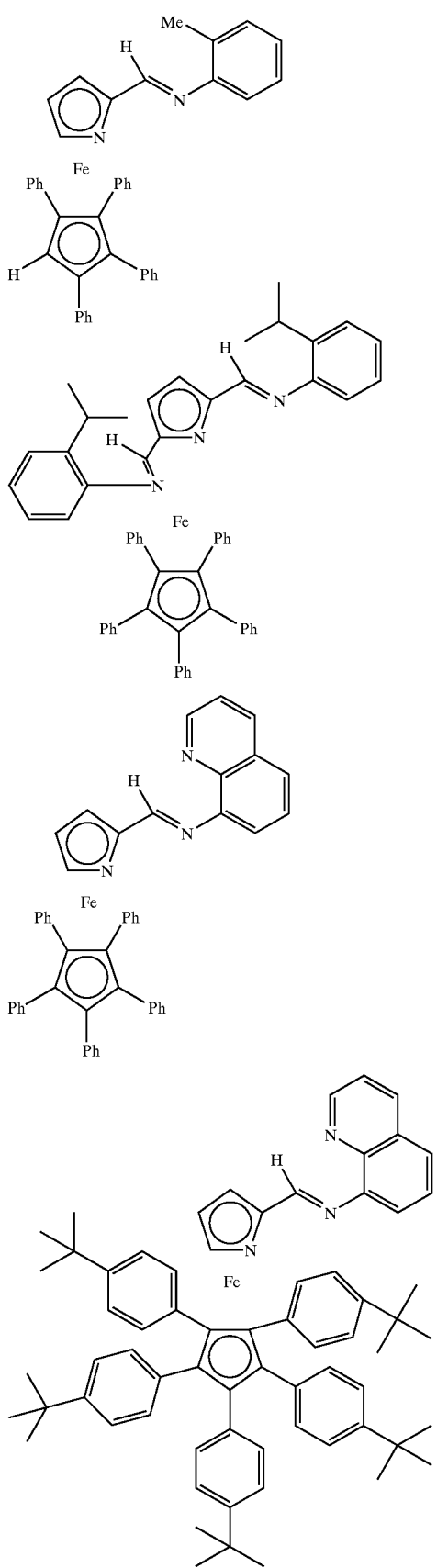
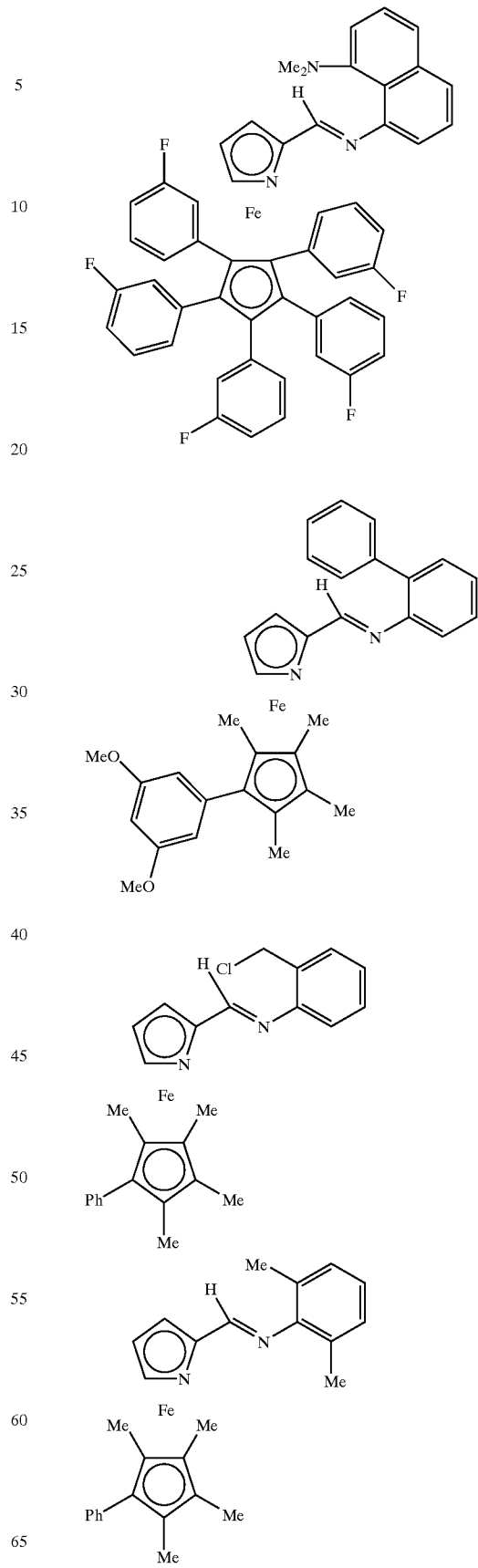

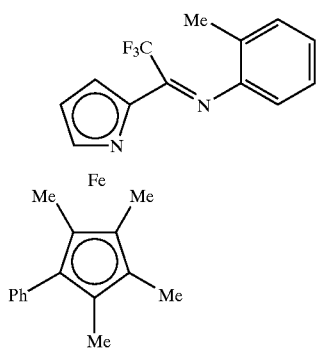

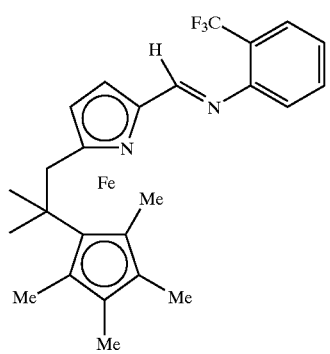

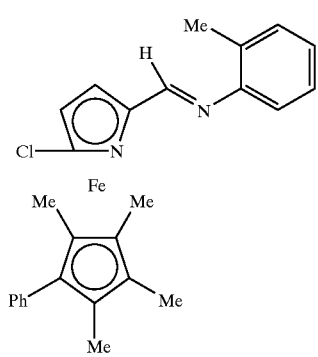

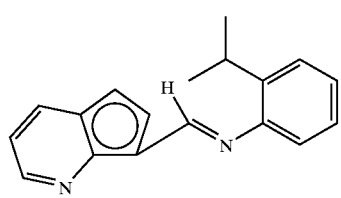

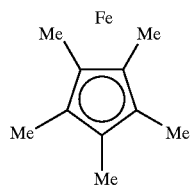

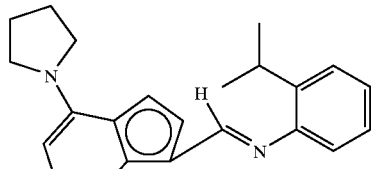

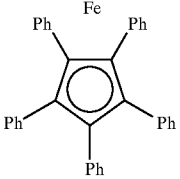

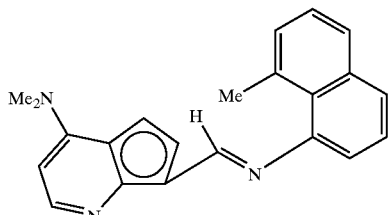

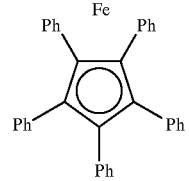

Among the coordinative compounds of formula (5) of the present invention, those in which A is a nitrogen atom can be synthesized from azaferrocene compounds represented by the following general formula (6):

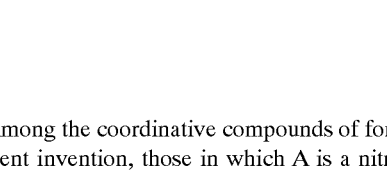

(6)

wherein $R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from nitrogen, oxygen, halogen and sulfur atoms and, when m is an integer of at least 2, $R^3$s may be the same as or different from each other, and adjacent $R^3$s may form together a ring;

$R^4$ represents a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group heaving a hydrocarbon group with 1 to 20 carbon atoms, or a hydrocarbon group having 1 to 20 carbon atoms and containing at least one atom selected from nitrogen, phosphorus, oxygen, halogen and sulfur atoms; and, when n is an integer of 1, $R^4$ is not a methyl group; and, when a is an integer of at least 2, $R^4$s may be the same as or different from each other, and all of the $R^4$s are not simultaneously a methyl group: and adjacent $R^4$s may form together a ring; and $R^3$ and $R^4$ may form together a ring; and m is an integer of 1 to 3 and n is an integer of 1 to 5.

As specific examples of the precursor azaferrocene compounds of formula (6), there can be mentioned compounds represented by the following formulae.

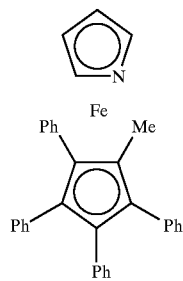

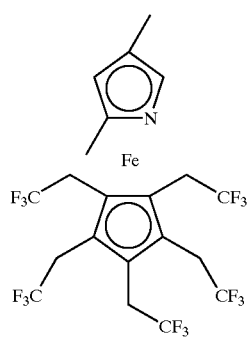

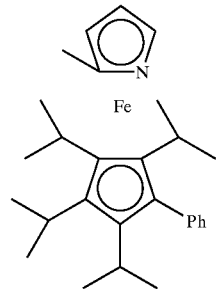

-continued

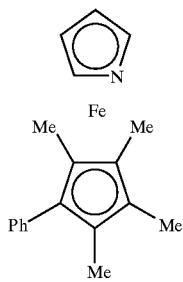

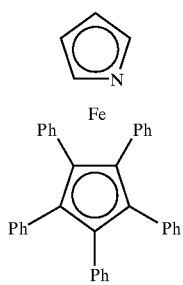

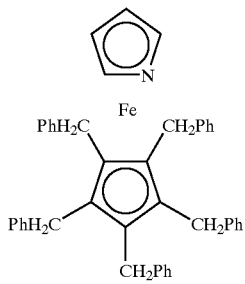

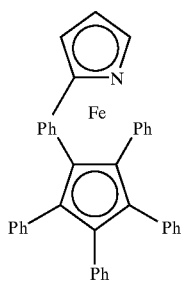

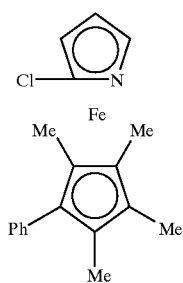

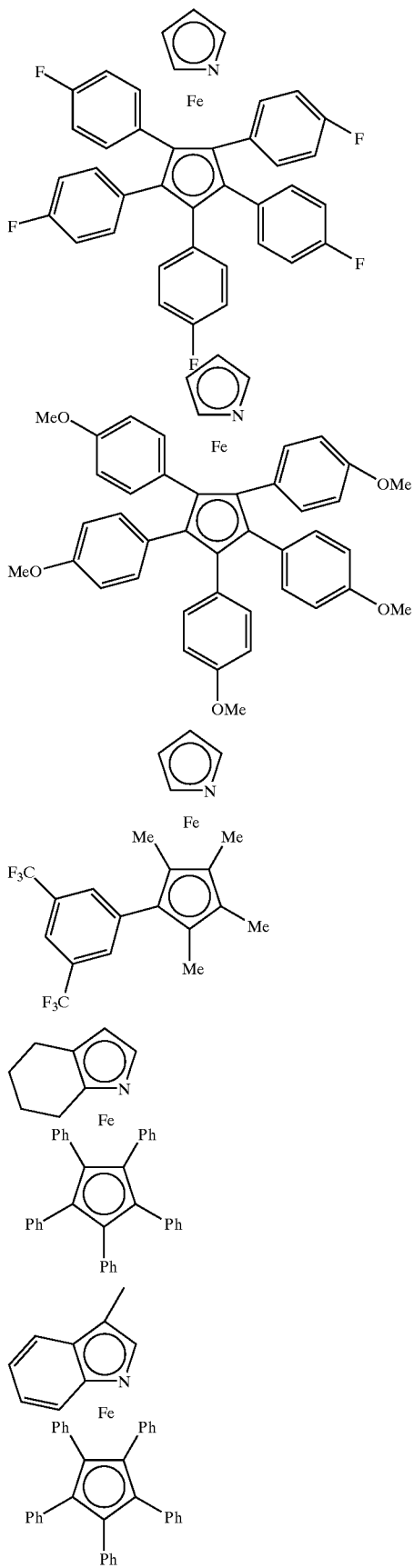
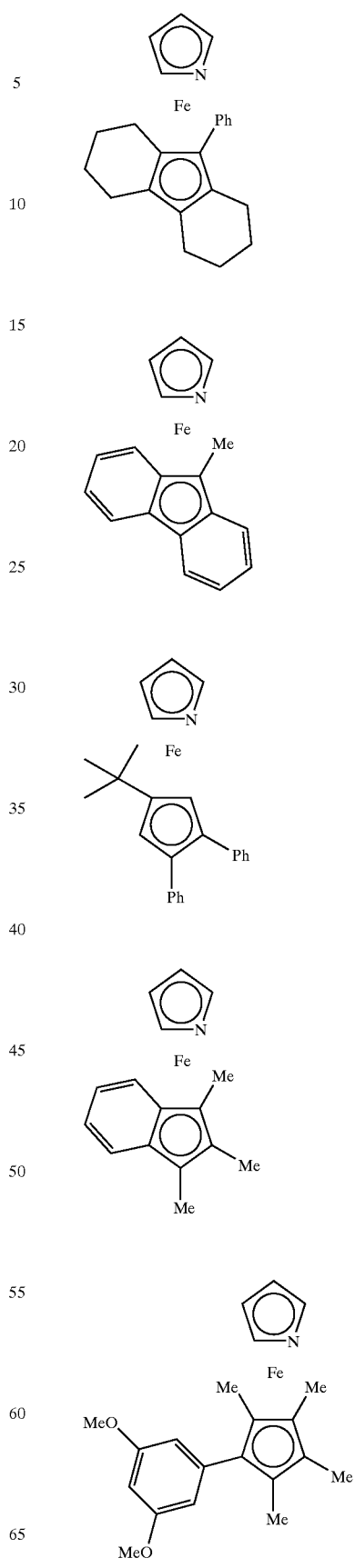

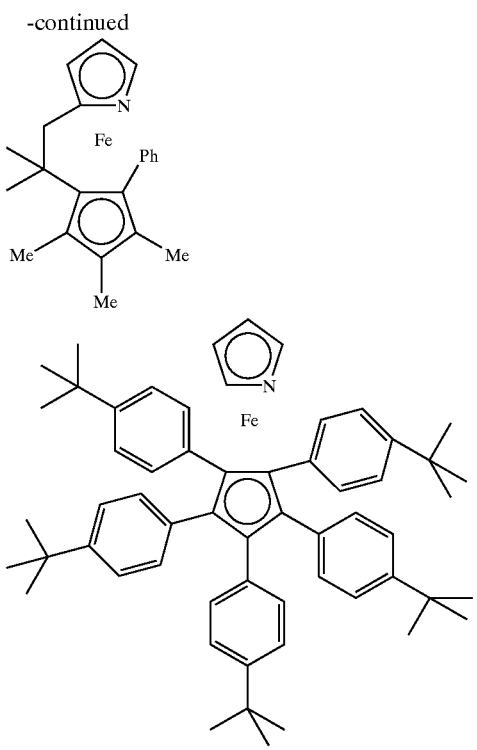

The azaferrocene compound of formula (6) according to the present invention can be synthesized by a process described in G. C. Fu et al, J. Org. Chem., vol. 61, p7230 (1996) or K. K. Joshi et al, J. Organomet. Chem., I, p471 (1964).

The coordinative compound of formula (5) according to the present invention can be synthesized from the azaferrocene compound of formula (6). For example, the azaferrocene compound of formula (6) is lithiated with a lithiating agent such as n-butyllithium, and then the obtained organolithium compound is allowed to react with, for example, N,N-dimethylformamide, benzonitrile or acetonitrile to introduce a carbonyl-containing group such as a formyl group or an acetyl group. The lithiation of the azaferrocene compound can be effected, for example, by a process described in V. N. Setkina et al, J. Organomet. Chem., vol. 251, C-p41 (1983). If the lithiation is carried out in the presence of a chiral diamine such as (−)-sparteine, then an azaferrocene compound predominantly comprised of one of the enantiomers, i.e., an optically active azaferrocene compound can be synthesized. The introduction of a carbonyl group-containing group can also be carried out by a Friedel-Crafts acylation using an acid chloride and aluminum chloride. The coordinative compound of formula (5) according to the present invention can also be synthesized by a process wherein the compound having introduced therein a carbonyl-containing group is subjected to dehydro-condensation with an aromatic amine or an aliphatic amine to be thereby converted to an imine. The imine-formation can be carried out by using acetic acid as a catalyst in ethanol or by using p-toluenesulfonic acid as a catalyst in toluene.

Coordinative compounds used as raw materials for producing the transition metal compound of formula (4) according to the present invention can be synthesized from a ferrocene derivative having a pyrindine ring. The ferrocene derivative having a pyrindine ring is prepared from pyrindine, for example, by a process described in G. C. Fu et al. J. Am. Chem. Soc., vol. 123, p353 (2001). The thus-prepared ferrocene having a pyrindine ring is lithiated with a lithiating agent such as n-butyllithium, and then the obtained organolithium compound is allowed to react with, for example, N,N-dimethylformamide, benzonitrile or acetonitrile to introduce a carbonyl-containing group such as a formyl group or an acetyl group. The introduction of a carbonyl group-containing group can also be carried out by a Friedel-Crafts acylation using an acid chloride and aluminum chloride. The coordinative compound of formula (5) according to the present invention can be synthesized by a process wherein the compound having introduced therein a carbonyl-containing group is subjected to dehydro-condensation with an aromatic amine or an aliphatic amine to be thereby converted to an imine. The imine-formation can be carried out by using acetic acid as a catalyst in ethanol or by using p-toluenesulfonic acid as a catalyst in toluene.

Among the coordinative compounds of the present invention represented by formula (5), those in which A is a carbon atom can be synthesized from a ferrocene derivative. A ferrocene compound having two cyclopentadienyl rings (hereinafter abbreviated to "Cp ring"), each of which has a substituent containing a hetero atom, is synthesized, for example, by a process wherein a formyl group is introduced in each Cp ring and then the formyl group-introduced ferrocene compound is subjected to dehydro-condensation with an amine whereby an imino group is introduced, which process is described in J. Organomet. Chem., vol. 412, p381 (1991) and Organometallics, vol. 18, p1267 (1999). A ferrocene compound having two cyclopentadienyl rings, at least one of which has two or more substituents, is synthesized, for example, by a heteroatom-introducing process as described in Bull. Chem. Soc., Jpn, vol. 53, p1138 (1980) and J. Org. Chem., vol. 62, p6733 (1997). By employing a combination of these processes, various substituents can be introduced into the two Cp rings. Further, an asymmetric ferrocene structure can be formed by using a specific reaction of a substituted cyclopentadienyl alkali metal as described in J. Organomet. Chem., vol. 598, p365 (2000).

The transition metal compound of the present invention, represented by formula (1), having the above-mentioned azaferrocene or ferrocene ligand can be synthesized by the conventional processes employed for synthesis of known complexes. For example, a process described in WO96/23010 and J. Am. Chem. Soc., vol. 121, p8728 (1999).

The transition metal compound of the present invention, represented by formula (1), having the above-mentioned azaferrocene or ferrocene ligand is used as a catalyst for polymerization of olefins. The transition metal compound can be used for the polymerization catalyst either after it is isolated by an ordinary procedure in the synthesis process, or as it is synthesized in-situ.

By the term "activating cocatalyst (B)" used in combination with the above-mentioned transition metal compound of the present invention, we mean a compound having a function of forming an activated species capable of polymerizing an olefin by a cooperative action or reaction with the transition metal compound or with a reaction product of the transition metal compound with an organometal compound. The activating cocatalyst provides a compound which weakly coordinates or exhibits cooperative activity for the thus-formed activated species, but does not directly react with the activated species.

The activating cocatalyst includes, for example, trialkylaluminums such as triethylaluminum and triisobutylaluminum; halogenated alkylaluminums such as diethylaluminum chloride and ethylaluminum sesquichloride; halogenated alkylaluminoxanes such as 1,3-dichloro-1,3-diethylaluminoxane and 1,3-dichloro-1,3-diisopropylaluminoxane; alkylaluminoxanes which have been recently widely used as a cocatalyst for a homogeneous polymerization catalyst system for olefins, ionized ionic compounds having a non-coordinative anion, and modified clay compounds. But, the activating cocatalyst should not be construed to be limited to these compounds.

As preferable examples of the alkylaluminoxane as the activating cocatalyst (B), there can be mentioned compounds represented by the following formulae (7) and (8):

(7)

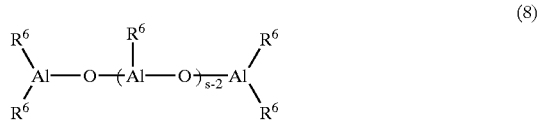

(8)

wherein $R^6$s may be the same or different and represents a hydrogen atom, or a hydrocarbon group having 1 to 20 carbon atoms such as methyl, ethyl, propyl and tert.-butyl groups, and s is an integer in the range of 2 to 60. The alkylaluminoxanes may be used either alone or in combination. The alkylaluminooxanes may contain a minor amount of an organometallic compound.

As preferable examples of the ionized ionic compounds having a non-coordinative anion as the activating cocatalyst, there can be mentioned protonic acids represented by the following general formula (9), ionized ionic compounds represented by the following general formula (10), Lewis acids represented by the following general formula (11), Lewis acidic compounds represented by the following general formula (12), and compounds having a structure of $AgSbF_6$ or $AgPF_6$.

[HL$^1$][B(Ar)$_4$]  (9)

[AL$^2{}_u$][B(Ar)$_4$]  (10)

[D][B(Ar)$_4$]  (11)

B(Ar)$_3$  (12)

wherein H is a proton, B is a boron atom or an aluminium atom, $L^1$ is a Lewis base, $L^2$ is a Lewis base or a cyclopentadienyl group, A is a cation of metal selected from lithium, iron and silver, D is a carbonium cation or a tropylium cation, Ar is a halogen-substituted aryl group having 6 to 20 carbon atoms, and u is an integer in the range of 0 to 2.

As specific examples of the protonic acids of formula (9), there can be mentioned diethyloxonium tetrakis[3,5-bis(trifluoromethyl)phenyl]borate, diethyloxonium tetrakis(pentafluorophenyl)borate, dimethyloxonium tetrakis(pentafluorophenyl)borate, tetramethyleneoxonium tetrakis(pentafluorophenyl)borate, hydronium tetrakis(pentafluorophenyl)borate, N,N-dimethylanilinium tetrakis(pentafluorophenyl)borate, tri-N-butylammonium tetrakis(pentafluorophenyl)borate, diethyloxonium tetrakis(pentafluorophenyl)aluminate, dimethyloxonium tetrakis(pentafluorophenyl)aluminate, tetramethyleneoxonium tetrakis(pentafluorophenyl)aluminate, hydronium tetrakis(pentafluorophenyl)aluminate, N,N-dimethylanilinium tetrakis-(pentafluorophenyl)aluminate and tri-N-butylammonium tetrakis(pentafluorophenyl)aluminate. The protonic acids of formula (9) are not limited to these compounds.

As specific examples of the ionized ionic compounds of formula (10), there can be mentioned sodium tetrakis[3,5-bis(trifluoromethyl)phenyl]borate; lithium salts such as lithium tetrakis(pentafluorophenyl)borate and lithium tetrakis(pentafluorophenyl)aluminate, and ether complexes thereof; ferrocenium salts such as ferrocenium tetrakis(pentafluorophenyl)borate and ferrocenium tetrakis(pentafluorophenyl)aluminate; and silver salts such as silver tetrakis(pentafluorophenyl)borate and silver tetrakis(pentafluorophenyl)aluminate. The ionized ionic compounds of formula (10) are not limited to these compounds.

As specific examples of the Lewis acids of formula (11), there can be mentioned trityl tetrakis(pentafluorophenyl)borate, trityl tetrakis(pentafluorophenyl)aluminate, tropylium tetrakis(pentafluorophenyl)borate and tropylium tetrakis(pentafluorophenyl)aluminate. The Lewis acids of formula (11) are not limited to these compounds.

As specific examples of the Lewis acidic compounds of formula (12), there can be mentioned tris[3,5-bis(trifluoromethyl)phenyl]borane, tris(pentafluorophenyl)borane, tris(2,3,5,6-tetrafluorophenyl)borane, tris(2,3,4.5-tetrafluorophenyl)-borane, tris(3,4,5-trifluorophenyl)borane, phenyl-bis(perfluorophenyl)borane and tris(3,4,5-trifluorophenyl)-aluminium. The Lewis acidic compounds of formula (12) are not limited to these compounds.

Preferable examples of the modified clay compound as the activating cocatalyst (B) are modified clay compounds having a cation exchangeability. The modification of the clay compounds for the activating cocatalyst is preferably effected by subjecting the clay compound to treatments such as a chemical treatment with an acid, an alkali or a salt, or a treatment with an organic compound or a inorganic compound to form a composite.

As specific examples of the clay compound, there can be mentioned natural clays including kaoline group such as kaolinite, dickite and halloysite; smectite group such as montmorillonite, hectrite, beidellite, saponites taeniolite and sauconite; mica group such as muscovite, paragonite and illite; vermiculite group; brittle mica group such as margarite and clinotnite; chlorite group such as donbassite, cookeite and clinochlore; sepiolite and palygorskite; and synthetic clay compounds. The modified clay compounds are not limited to these compounds.

The treating agents used for a chemical treatment of the clay compounds include, for example, acids including brønsted acids such as hydrochloric acid, sulfuric acid, nitric acid and acetic acid; alkalis such as sodium hydroxide, potassium hydroxide and calcium hydroxide; and salts including inorganic salts which include ionic chlorides such as sodium chloride, potassium chloride, lithium chloride, magnesium chloride, aluminum chloride, iron chloride and ammonium chloride, sulfates such as sodium sulfate, potassium sulfate, aluminum sulfate and sodium sulfate, carbonates such as potassium carbonate, sodium carbonate and calcium carbonate, and phosphates such as sodium phosphate, potassium phosphate, aluminum phosphate and ammonium phosphate, and organic acid salts such as sodium acetate, potassium acetate, potassium oxalate, sodium citrate and sodium tartrate.

The organic compound used for treating the clay compound to form an organic composite includes, for example, onium salts, carbon cation-forming compounds such as trityl chloride and tropylium bromide, metal complex cation-forming complex compounds such as ferrocenium salts. The inorganic compound used for treating the clay compound to form an inorganic composite includes, for example, hydroxide cation-forming metal hydroxides such as aluminum hydroxide, zirconium hydroxide and chromium hydroxide.

Among the modified clay compounds used in the present invention, an especially preferable modified clay compound is a clay compound/organic ion composite which is produced by a metal ion, i.e., an exchangeable cation, present within the clay compound is exchanged with a specific organic cation. As specific examples of the organic cation, there can be mentioned ammonium ions including aliphatic ammonium cations such as butylammonium, hexylammonium, decylammonium, dodecylammonium, dialkylammonium, tributylammonium and N,N-dimethyldexylammonium; and aromatic ammonium cations such as anilinium, N-methylanilinium, N,N-dimethylanilinium, N-ethylanilinium, N,N-diethylanilinium, benzylammonium, toluidinium, dibenzylammonium, tribenzylammonium and N,N,2,4,6-pentamethylanilinium; and oxonium ions such as dimethyloxonium and diethyloxonium. The organic cations used are not limited to these cations.

The activating cocatalyst (B) used as an ingredient of the catalyst for polymerization of olefins of the present invention can also be topotactic reduction products accompanied by transfer of electrons. Such reduction product include, for example, compounds represented by the following formula (13):

wherein [G] is a host compound, k is a quantity of reduction, $E^{r+}$ is a guest cation with a valency of n, $L^3$ is a Lewis base, and h is a quantity of Lewis base.

The host compound [G] includes, for example, host compounds having a three-dimensional structure, host compounds having a two-dimensional structure, host compounds having a one-dimensional structure, and host compounds which are molecular solid.

As specific examples of the host compounds having a three-dimensional structure, there can be mentioned hexamolybdenum octasulfide, divanadium pentaoxide, tungsten trioxide, titanium dioxide, vanadium dioxide, chromium dioxide, manganese dioxide, tungsten dioxide, ruthenium dioxide, osmium dioxide and iridium dioxide.

As specific examples of the host compounds having a two-dimensional structure, there can be mentioned titanium disulfide, zirconium disulfide, hafnium disulfide, vanadium disulfide, niobium disulfide, tantalum disulfide, chromium disulfide, molybdenum disulfide, tungsten disulfide, rhenium disulfide, platinum disulfide, tin disulfide, lead disulfide, phosphomagnesium trisulfide, phosphomanganese trisulfide, tantalum sulfide carbide, molybdenum trioxide, vanadium pentaoxide gel, graphite and polyacene.

As specific examples of the host compounds having a one-dimensional structure, there can be mentioned titanium trisulfide and niobium triselenide.

As specific examples of the molecular solid host compounds, there can be mentioned tetracyanoquinodimethane and tetrathiofulvalene.

As the [G], a mixture of two or more of the above-mentioned host compounds can be used.

The value k is not particularly limited, but, in view of enhanced catalytic activity for polymerization of olefins, k is preferably In the range of $0<k \leq 3$, and more preferably $0<k \leq 2$.

The $L^3$ includes Lewis bases capable of coordinating to $E^{r+}$ and a cyclopentadienyl group. As specific examples of the Lewis bases, there can be mentioned water, amine compounds, nitrogen-containing heterocyclic compounds, ethers such as ethyl ether and n-butyl ether, amides such as formamide, N-methylformamide and N-methylacetamide, alcohols such as methyl alcohol and ethyl alcohol, and diols such as 1,2-butanediol and 1,3-butanediol. These bases may be used either alone or as a mixture of at least two thereof. The value h can be in the range of $0 \leq h \leq 10$.

The guest cation $E^{r+}$ includes cations containing at least one atom selected from atoms of group 1 to group 14 of the periodic table, and r is in the range of $0<r \leq 10$. In view of enhanced catalytic activity for polymerization of olefins, as preferable examples of the guest cation $E^{r+}$, there can be mentioned cations represented by the following formulae (14) and (15).

Wherein $R^7_2R^8N$ is an amine compound, and $R^7$ independently represents a hydrogen atom or an aliphatic hydrocarbon group having 1 to 30 carbon atoms and $R^8$ is a hydrogen atom, an aliphatic hydrocarbon group having 1 to 30 carbon atoms or an aromatic hydrocarbon group having 6 to 50 carbon atoms.

wherein $(R^9)^+$ is a carbonium cation or tropylium cation, which have 1 to 50 carbon atoms. These guest cations may be used either alone or in combination.

As specific examples of the amine compound represented by formula $R^7_2R^8N$, there can be mentioned aliphatic amines such as methylamine, n-propylamine, isopropylamine, n-butylamine, tert.-butylamine, allylamine, N-methylcyclohexylamine, N,N-dimethyloctylamine, N,N-dimethyldodecylamine, N,N-dimethyloctadecylamine, N,N-dioctadecylmethylamine, trihexylamine, triisooctylamine, tridodecylamine and N,N-dimethylcyclohexylamine; and aromatic amines such as aniline, N-methylaniline, N-ethylaniline, N-allylaniline, o-toluidine, p-toluidine, N,N-dimethylaniline, N-methyl-o-toluidine, N-methyl-m-toluidine and N-ethyl-o-toluidine.

As specific examples of the cation of formula (15), there can be mentioned a triphenylmethyl cation and a tropylium cation.

The polymerization of olefins using the catalyst of the present invention can be carried out by ordinary polymerization procedures such as slurry polymerization, vapor phase polymerization, high-pressure polymerization, solution polymerization and bulk polymerization. By the term "polymerization" used herein, we mean not only homopolymerization for producing a homopolymer but also copolymerization for producing a copolymer.

The catalyst of the present invention comprising the above-mentioned transition metal compound and the above-mentioned activating cocatalyst can be used in combination with an organometallic compound. The organometallic compound is preferably a compound having a function of deactivating ingredients forming a catalyst poison, and capable of forming an alkyl moiety of the transition metal compound. As specific examples of the organometallic compound, there can be mentioned alkyllithium compounds such as methyllithium and n-butyllithium; Grignard reagents such as methylmagnesium chloride, ethylmagnesium chloride, isopropylmagnesium chloride, benzylmagnesium chloride, methylmagnesium bromide, ethylmagnesium bromide, isopropylmagnesium bromide and benzylmagnesium bromide; dialkylmagnesiums such as dimethylmagnesium; dialkylzincs such as dimethylzinc and diethylzinc; alkylboranes such as trimethylborane and triethylborane, alkylaluminums such as trimethylaluminum, triethylaluminum and triisobutylaluminum; and alkylaluminoxanes such as methylaluminoxane, butylaluminoxane and tert.-butylaluminoxane.

As specific examples of the olefin to be polymerized in the presence of the catalyst of the present invention, there can be mentioned α-olefins such as ethylene, propylene, 1-butene, 4-methyl-1-pentene, 1-hexene and 1-otene; styrene and styrene derivatives; conjugated dienes and non-conjugated dienes such as butadiene, 1,4-hexadiene, 5-ethylidene-2-norbornene, dicyclopentadiene, 4-methyl-1,4-hexadiene and 7-methyl-1,6-octadiens; cycloolefins such as cyclobutene and cyclohexene; α,β-unsaturated carboxylic acids such as acrylic acid, methacrylic acid, fumaric acid, maleic anhydride, itaconic acid, itaconic anhydride and bicyclo(2,2,1)-5-heptene-2,3-dicarboxylic acid; metal salts of α,β-unsaturated carboxylic acids such as sodium, potassium, lithium, zinc, magnesium and calcium salts of the above-recited α,β-unsaturated carboxylic acids; esters of α,β-unsaturated carboxylic acids such as methyl acrylate, ethyl acrylate, isopropyl acrylate, butyl acrylate, isobutyl acrylate, t-butyl acrylate, 2-ethylhexyl acrylate, methyl methacrylate, ethyl methacrylate, n-propyl methacrylate, isopropyl methacrylate, n-butyl methacrylate and isobutyl methacrylate; vinyl esters such as vinyl acetate, vinyl propionate, vinyl caproate, vinyl caprylate, vinyl laurate, vinyl stearate and vinyl trifluoroacetate; unsaturated glycidyl esters such as glycidyl acrylate, glycidyl methacrylate, glycidyl itaconate and monoglycidyl itaconate; vinyl ketones such as methyl vinyl ketone, ethyl vinyl ketone and phenyl vinyl ketone; α,β-unsaturated nitriles such as acrylonitrile, methacrylonitrile and 1-phenylacrylonitrile. These olefins may be polymerized as a mixture of at least two thereof, such as ethylene plus propylene, ethylene plus 1-butene, ethylene plus 1-hexene, ethylene plus 1-octene, ethylene plus vinyl acetate, ethylene plus methyl acrylate, ethylene plus methyl methacrylate, ethylene plus propylene plus styrene, ethylene plus 1-hexene plus styrene, and ethylene plus propylens plus ethylidene norbornene.

The polymerization of an olefin can be carried out in the vapor phase or the liquid phase. The liquid medium used in the liquid phase polymerization is not particularly limited and may be selected from those which are generally used. The liquid medium includes, for example, benzene, toluene, xylone, pentane, hexane, heptane, 2,2,2-trifluoroethanol and hexafluoroisopropyl alcohol. Olefins themselves such as proplylens, 1-butene, 1-octene and 1-hexene may be used as the liquid medium.

The polymerization conditions employed for polymerization of olefins are not particularly limited, but preferably, the polymerization temperature is in the range of –100° C. to 300° C., the polymerization time is in the range of 10 seconds to 60 hours, and the polymerization pressure is in the range of normal pressure to 3,000 kg/cm$^2$G. At polymerization, the molecular weight can be controlled by using hydrogen. The polymerization procedure can be any of batchwise, semi-continuous and continuous manners. The polymerization can be carried out in two stages under different polymerization conditions. Olefin polymers are separated for recovery from a polymerization mixture and dried by a conventional procedure.

The benefits of the present invention can be summarized as follows. The transition metal compound having an azaferrocene or ferrocene structure of the present invention can be easily synthesized and various substituents can be introduced therein. The transition metal compound exhibits a high catalytic activity for polymerization of olefins, and olefins can be polymerized with an enhanced efficiency by using the catalyst. It is presumed that the transition metal compound having an azaferrocene or ferrocene structure of the present invention can be used as a catalyst for synthesis of polycarbonate and for asymmetric synthesis, for example, asymmetric cyclopropane synthesis, as well as a catalyst for polymerization olefins.

The invention will now be described by the following working examples that by no means limit the scope of the invention.

In the working examples, transition metal compounds were synthesized by using a Schlenk technique or dry box, and all operations were carried out in an argon or nitrogen atmosphere. The solvents used for the preparation of the transition metal compounds were subjected to deoxygen treatment and dehydration treatment by the conventional procedure prior to the use thereof. The polymerization reaction was carried out by using an autoclave at a predetermined temperature for a predetermined time while ethylene gas was continuously fed therein. The polymerization mediums used for polymerization were subjected to deoxygen treatment and dehydration treatment by the conventional procedure prior to the use for polymerization. As the ethylene gas, that of polymerization grade was used.

EXAMPLE 1

Synthesis of Complex A-1

Synthesis of Coordinative Compound

By the method described in J. Org. Chem., vol. 62, p6733 (1997), 1,2-diformylferrocene was synthesized.

The atmosphere within a 50 ml Schlenk flask was replaced with nitrogen, and, 625 mg (2.58 mmol) of 1,2-diformylferrocene was dissolved in 8 ml of ethanol in the flask. Then 493 mg (5.29 mmol) of aniline was added to the obtained solution, and the mixture was stirred at room temperature overnight to conduct a reaction. After completion of the reaction, the reaction mixture was distilled under a reduced pressure to remove ethanol. To the obtained solid residue, 20 ml of cyclohexane was added to carry out recrystallization. The precipitated crystal was filtered and dried under a reduced pressure to give 620 mg (1.58 mmol) of a deep red solid. The yield was 61%.

$^1$H-NMR (400 MHz, C$_6$D$_6$) δ=3.99 (s, 5H), 4.25 (t, J=2.6 Hz, 1H), 5.02 (d. J=2.6 Hz, 2H), 7.02–7.28 (m, 10H), 8.91 (s, 2H).

MS m/z 392 (M$^+$).

Synthesis of Complex A-1

The atmosphere within a 50 ml Schlenk flask was replaced with nitrogen, and, 143 mg (0.539 mmol) of (1,5-cyclooctadiene)PdMeCl and 219 mg (0.558 mmol) of the ligand prepared by the above-mentioned procedure were placed therein. Then 6 ml of toluene was added in the flask. The mixture was stirred at room temperature for 20 hours to conduct a reaction. Then the reaction mixture was concentrated under a reduced pressure and then washed with 2 ml of toluene. The obtained residue was dried under a reduced pressure to give 254 mg (0.497 mmol) of a red solid (complex A-1). The yield was 89%.

$^1$H-NMR (400 MHz, CD$_2$Cl$_2$) δ=0.14 (s, 3H), 4.39 (s, 5H), 5.12 (brs, 1H), 5.22 brs, 2H), 7.10–7.55 (m, 6H), 7.65–7.83 (m, 4H), 8.56 (s, 1H), 8.59 (s, 1H).

MS m/z 549 (M$^+$).

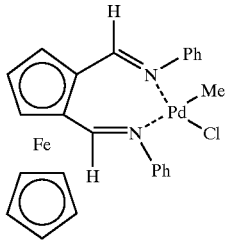

EXAMPLE 2

Synthesis of Complex A-2

The atmosphere within a 50 ml Schlenk flask was replaced with nitrogen, and, 204 mg (0.371 mmol) of Complex A-1, prepared in Example 1, and 129 mg (0.375 mmol) of AgSbF$_6$ were placed therein. The content was cooled to −50° C., and a solution of 0.15 ml of acetonitrile in 6 ml of dichloromethane was dropwise added. The temperature was elevated to −10° C. over a period of 4 hours, and then obtained slurry was filtered and the extracted with dichloromethane. The combined dichloromethane solutions were concentrated under a reduced pressure. The obtained solid residue was dissolved in 4 ml of dichloromethane, and then 9 ml of pentane was dropwise added. A clear supernatant liquid was removed, and the obtained residue was dried under a reduced pressure to give 291 mg (0.368 mol) of a deep red solid (complex A-2). The yield was 99%.

$^1$H-NMR (400 MHz, CD$_2$Cl$_2$) δ=0.33 (s, 3H), 1.95 (s, 3H), 4.47 (s, 5H), 5.28 (brs, 1H), 5.37 (brs, 1H), 5.45 (brs, 1H), 7.42–7.75 (m, 10H), 8.60 (s, 1H), 8.73 (s, 1H). MS m/z 790 (M$^+$).

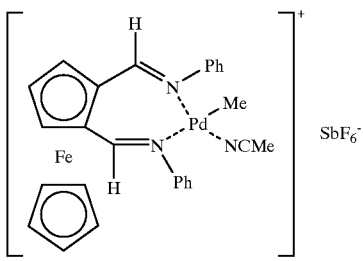

EXAMPLE 3

Synthesis of Complex A-3

The atmosphere within a 50 ml Schlenk flask was replaced with nitrogen, and, 90 mg (0.163 mmol) of complex A-1, prepared in Example 1, and 165 mg (0.187 mmol) of sodium tetrakis[3,5-bis(trifluoromethyl)phenyl]borate were placed therein. The content was cooled to −50° C., and a solution of 0.09 ml of acetonitrile in 5 ml of dichloromethane was dropwise added. The temperature was elevated to −10° C. over a period of 4 hours, and the obtained slurry was filtered and then extracted with dichloromethane. The combined dichloromethane solutions were concentrated under a reduced pressure. The obtained solid residue was dissolved in 3 ml of diethyl ether, and then 4 ml of pentane was dropwise added. A clear supernatant liquid was removed, and the obtained residue was dried under a reduced pressure to give 135 mg (0.095 mmol) of a deep red solid (complex A-3). The yield was 58%.

$^1$H-NMR (400 MHz, CD$_2$Cl$_2$) δ=0.34 (s, 3H), 1.90 (s, 3H), 4.47 (s, 5H), 5.25 (s, 1H), 5.49 (s, 1H), 5.64 (s, 1H), 7.40–7.67 (m, 10H), 7.58 (s, 4H), 7.73 (s, 8H), 8.58 (s, 1H), 8.69 (s, 1H).

MS m/z 1418 (M$^+$).

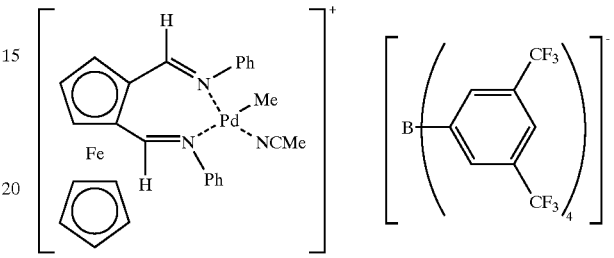

EXAMPLE 4

Synthesis of Complex A-4

The atmosphere within a 50 ml Schlenk flask was replaced with nitrogen, and, 115 mg (0.373 mmol) of (dimethoxyethane)NiBr$_2$ and 3 ml of dichloromethane were placed therein. To the thus-obtained suspension, a solution of 153 mg (0.390 mmol) of the ligand prepared in Example 1, in 5 ml of dichloromethane was added. The mixture was stirred at room temperature over a period of 3 hours, and the reaction mixture was filtered and extracted with dichloromethane. The combined dichloromethane solutions were concentrated under a reduced pressure. The obtained solid residue was washed with 40 ml of cyclohexane, and dried under a reduced pressure to give 213 mg (0.348 mmol) of a deep red solid (complex A-4). The yield was 93%.

MS m/z 610 (M$^+$).

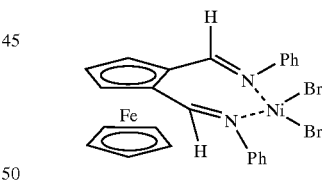

EXAMPLE 5

Synthesis of Complex B-1

Synthesis of Coordinative Compound

By the method described in J. Organomet. Chem., vol. 412, p381 (1991), 1,1'-diformylferrocene was synthesized.

The atmosphere within a 50 ml Schlenk flask was replaced with nitrogen, and, the flask was charged with 1.04 g (4.30 mmol) of 1,1'-diformylferrocene, 5 g of molecular sieves 4A, 8 ml of toluene and 1.26 g (17.2 mmol) of tert.-butylamine. The content was stirred at room temperature for 15 hours to conduct a reaction. The reaction mixture was distilled under a reduced pressure to remove volatile ingredients. The residue was extracted with 20 ml of diethyl ether, and the extracted material was concentrated and dried under a reduced pressure to give 1.35 g (3.83 mmol) of a brown solid. The yield was 89%.

$^1$H-NMR (400 MHz, C$_6$D$_6$) δ=1.30 (s, 18H), 4.12 (t, J=2.2 Hz, 4H), 4.64 (t, J=2.2 Hz, 4H), 8.05 (s, 2H).

MS m/z 352 (M$^+$).

Synthesis of Complex B-1

The atmosphere within a 50 ml Schlenk flask was replaced with nitrogen, and, 120 mg (0.452 mmol) of (1,5-cyclooctadiene)PdMeCl and 156 mg (0.443 mmol) of the ligand prepared by the above-mentioned procedure were placed therein. Then 2.5 ml of toluene was added. The mixture was stirred at room temperature for 7 hours to conduct a reaction. Then the obtained slurry was filtered and then washed with 3 ml of toluene. The obtained residue was dried under a reduced pressure to give 135 mg (0.265 mmol) of a testaceous solid (complex B-1). The yield was 60%.

$^1$H-NMR (400 MHz, CD$_2$Cl$_2$) δ=0.55 (s, 3H), 1.72 (s, 18H), 4.55 (brs, 4H), 4.82 (brs, 2H), 6.02 (brs, 2H), 8.15 (s, 1H), 8.70 (brs, 1H).

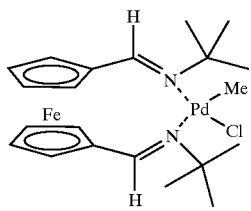

EXAMPLE 6

Synthesis of Complex B-2

Synthesis of Coordinative Compound

The atmosphere within a 50 ml Schlenk flask was replaced with nitrogen, and, the flask was charged with 1.00 g (4.13 mmol) of 1,1'-diformylferrocene, 25 ml of ethanol, 1.26 g (10.4 mmol) of 2,6-dimethylaniline and 10 mg of acetic acid. The content was stirred for 8 hours under heated reflux conditions to conduct a reaction. The reaction mixture was distilled under a reduced pressure to remove volatile ingredients. The residue was extracted with 90 ml of diethyl ether, and the extracted material was concentrated under a reduced pressure. The obtained solid was recrystallized from hexane/toluene (5/1), and then filtered and dried to give 0.90 g (2.00 mmol) of an orange-colored solid. The yield was 49%.

$^1$H-NMR (400 MHz, C$_6$D$_6$) δ=2.20 (s, 12H), 4.23 (t, J=2.2 Hz, 4H), 4.70 (t, J=2.2 Hz, 4H), 6.96 (t, J=7.8 Hz, 2H), 7.05 (d, J=7.8 Hz, 4H), 7.70 (s, 2H).

MS m/z 448 (M$^+$).

Synthesis of Complex B-2

The atmosphere within a 50 ml Schlenk flask was replaced with nitrogen, and, 148 mg (0.479 mmol) of (dimethoxyethane)NiBr$_2$ and 3 ml of dichloromethane. To the suspension, a solution of 222 mg (0.495 mmol) of the ligand prepared by the above-mentioned procedure, in 5 ml of dichloromethane was added. The mixture was stirred at room temperature for 48 hours to conduct a reaction. Then the obtained slurry was filtered and then extracted with dichloromethane. The combined dichloromethane solutions were concentrated under a reduced pressure. The obtained residue was washed with 20 ml of toluene, and then dried under a reduced pressure to give 142 mg (0.213 mmol) of a deep red solid (complex B-2). The yield was 45%.

MS m/z 667 (M$^+$).

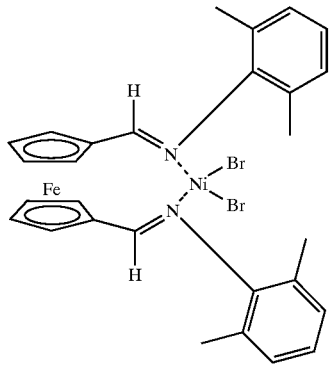

EXAMPLE 7

Preparation of Complex Solution

The atmosphere within a 100 ml of Schlenk flask was replaced with nitrogen, and the flask was charged with 59 mg (0.097 mol) of complex A-4 synthesized in Example 4, and 40 ml of toluene. The content was stirred for 30 minutes to prepare a complex solution.

Polymerization of Ethylene

Two liter autoclave was charged with 500 ml of toluene, and methylaluminoxane (PMAO available from Tosoh Akzo K.K., in an amount of 3.5 ml [equivalent to 10 mmol of aluminum atom]). The temperature within the autoclave was adjusted to 40° C., and ethylene was blown therein to a pressure of 10 kg/cm$^2$G. The complex solution prepared by the above-mentioned procedure was pressed into the autoclave, and polymerization was carried out at 40° C. for 1 hour while ethylene was continuously fed therein at a rate such that the pressure of 10 kg/cm$^2$G was maintained. The thus-obtained reaction liquid was treated by the ordinary procedure to obtain 12.8 g of a liquid polymer.

EXAMPLE 8

Polymerization of Ethylene 100 milli-liter glass autoclave was charged with 50 ml of toluene, and 33.4 mg (0.055 mmol) of complex A-4 prepared in Example 4. Ethylene was blown therein to a pressure of 10 kg/cm$^2$G. Then 4 ml of a solution containing 2.9% by weight (0.16 mmol) of tris(pentafluorophenyl)borane in Isopar-E (available from Tosoh Akzo K.K.) and 0.07 ml of a solution containing 20% by weight (0.17 mmol) of trimethylaluminum in toluene were added, and polymerization was carried out at room temperature for 2 hour while ethylene was continuously fed therein at a rate such that the pressure of 10 kg/cm$^2$G was maintained. The thus-obtained reaction liquid was treated by the ordinary procedure to obtain 1.1 g of a liquid polymer.

EXAMPLE 9

Preparation of Complex Solution

The atmosphere within a 100 ml of Schlenk flask was replaced with nitrogen, and the flask was charged with 69 mg (0.11 mmol) of complex A-4 synthesized in Example 4, and 50 ml of toluene. The content was stirred for 30 minutes to prepare a complex solution.

Copolymerization of Ethylene/Methyl Acrylate

Two liter autoclave was charged with 450 ml of toluene, and methylaluminoxane (PMAO available from Tosoh Akzo K.K., in an amount of 4.0 ml [equivalent to 12.8 mmol of aluminum atom]). Ethylene was blown therein to a pressure of 10 kg/cm$^2$G. The complex solution prepared by the above-mentioned procedure was pressed into the autoclave, and the mixture was stirred for 5 minutes. Then a solution of 5 ml (56 mmol) of methyl acrylate and 0.5 ml of methylaluminoxane in 40 ml of toluene was pressed into the autoclave, and then polymerization was carried out at room temperature for 24 hours while ethylene was continuously fed therein at a rate such that the pressure of 10 kg/cm$^2$G was maintained. The thus-obtained reaction liquid was quenched with 350 ml of 0.1N hydrochloric acid, and separated into two phases. The organic phase was washed with water. Then the organic phase was concentrated under a reduced pressure. The thus-obtained material was extracted with hexane. The extract was concentrated under a reduced pressure to give 1.82 g of a viscous copolymer liquid.

$^1$H-NMR (CDCl$_3$) revealed that the content of methyl acrylate units in the copolymer was 19% by weight. Gel permeation chromatography (GPC) revealed that the copolymer had a weight average molecular weight (Mw) of $1.0 \times 10^3$ and a Mw/number average molecular weight (Mn) ratio of 1.8.

EXAMPLE 10

Copolymerization of Ethylene/Methyl Acrylate

The procedures in Example 9 were repeated wherein 67 mg of complex A-4 and 15 ml of methyl acrylate were used with all other conditions remaining the same. Thus 1.25 g of a viscous copolymer liquid was obtained.

$^1$H-NMR (CDCl$_3$) revealed that the content of methyl acrylate units in the copolymer was 50% by weight. GPC revealed that the copolymer had a Mw of $1.0 \times 10^3$ and a Mw/Mn ratio of 1.9.

EXAMPLE 11

Polymerization of Ethylene

The procedures in Example 7 were repeated wherein 59 mg (0.088 mmol) of complex B-2 and 3.1 ml of methylaluminoxane (PMAO available from Tosoh Akzo K.K., equivalent to 8.8 mmol of aluminum atom]). All other conditions remained the same. Thus, 44 mg of a solid polymer was obtained. The polymer had a melting point of 124.4° C.

EXAMPLE 12

Synthesis of Complex C-1

Synthesis of Coordinative Compound

By the method described in J. Org. Chem., vol. 61, p7230 (1996), 1',2',3',4',5'-pentamethylazaferrocene was synthesized.

The atmosphere within a 50 ml Schlenk flask was replaced with nitrogen, and, 404 mg (1.57 mmol) of 1',2', 3',4',5'-pentamethylazaferrocene was dissolved in 7 ml of diethyl ether in the flask. Then 740 mg (3.10 mmol) of (−)-sparteine was added to the obtained solution, and then 2 ml (3.2 mmol) of 1.59 M n-BuLi solution in hexane was dropwise added under ice-cooled conditions. The content was stirred for 1 hour under ice-cooled conditions, and then 240 mg (3.3 mmol) of N,N-dimethylformamide was added. When 20 minutes elapsed, water was added to quench the reaction mixture. The reaction mixture was extracted with diethyl ether, and then, the organic phase was concentrated under a reduced pressure and the obtained residue was purified by silica gel column chromatography (solvent: hexane/ethyl acetate). Thus 350 mg (1.22 mmol) of a deep red liquid was obtained. The yield was 78%.

$^1$H-NMR (400 MHz, C$_6$D$_6$) δ=1.59 (s, 15H), 3.99 (s, 1H), 4.63 (s, 1H), 4.99 (s, 1H), 10.1 (s, 1H).

The atmosphere within a 50 ml Schlenk flask was replaced with nitrogen, and, the flask was charged with 341 mg (1.19 mmol) of 2-formylazaferrocene prepared by the above-mentioned procedure and 7 ml of ethanol. Then 140 mg (1.31 mmol) of o-toluidine and 10 mg of acetic acid were added. The content was stirred at room temperature for 2 days, and the reaction mixture was concentrated under a reduced pressure. The obtained residue was extracted with hexane, and the extract was concentrated under a reduced pressure to give 455 mg of a deep red liquid (coordinative compound).

$^1$H-NMR (400 MHz, C$_6$D$_6$) δ=1.72 (s, 15H), 2.58 (s, 3H), 4.07 (s, 1H), 4.92 (s, 1H), 5.06 (s, 1H), 6.90–7.40 (m, 4H), 8.54 (s, 1H).

Synthesis of Complex C-1

The atmosphere within a 50 ml Schlenk flask was replaced with nitrogen, and, 152 mg (0.49 mmol) of (DME) NiBr$_2$ and 2 ml of dichloromethane were placed therein. With stirring, a solution of 191 mg of the above-mentioned coordinative compound in 6 ml of dichloromethane was added by using a cannula. The content was stirred at room temperature for 2 hours, and the obtained reaction liquid (slurry) was filtered. The obtained solid was washed with dichloromethane and then the residue was dried under a reduced pressure to give 210 mg (0.35 mmol) of a red solid (complex C-1). The yield was 71%.

$^1$H-NMR (400 MHz, CD$_2$Cl$_2$) δ=−8.15 (s, 1H), −7.70 (s, 1H), −1.80 (s, 1H), 1.48 (s, 15H), 1.80 (s, 3H), 16.50 (s, 1H), 22.85 (s, 1H), 23.30 (s, 1H), 34.10 (s, 2H).

FAB-MASS: m/z 593 (M$^+$), 513 (M$^+$-Br), 433 (M$^+$-2Br), 374 (M$^+$-NiBr$_2$).

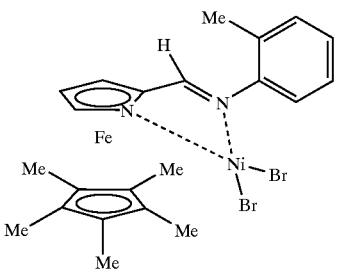

EXAMPLE 13

Synthesis of Complex C-2

The atmosphere within a 50 ml Schlenk flask was replaced with nitrogen, and, 43.8 mg (0.35 mmol) of iron(II)

chloride and 7 ml of tetrahydrofuran (THF) were placed therein. With stirring, a solution of 157 mg (0.42 mmol) of the coordinative compound, synthesized in Example 12, in 10 ml of THF was added by using a cannula. The content was stirred at room temperature for 2 hours, and the obtained reaction liquid (slurry) was filtered. The obtained solid was washed with THF and then the residue was dried under a reduced pressure to give 124 mg (0.25 mmol) of an orange-red solid (complex C-2). The yield was 71%.

FAB-MASS: m/z 465 ($M^+$-Cl), 429 ($M^+$-2Cl), 374 ($M^+$-$FeCl_2$).

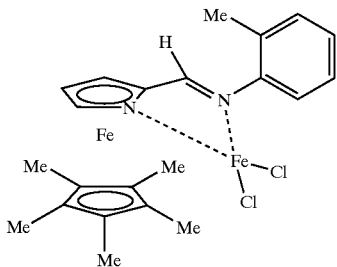

EXAMPLE 14 synthesis of Complex C-3

The Atmosphere within a 50 ml Schlenk flask was replaced with nitrogen, and, 45.9 mg (0.32 mmol) of copper (II) chloride and 10 ml of THF were placed therein. With stirring, a solution of 133 mg (0.36 mmol) of the coordinative compound, synthesized in Example 12, in 12 ml of THF was added by using a cannula. The content was starred at room temperature for 2 hours, and the obtained homogeneous black reaction liquid was preserved over night in a freezer. Then the liquid was filtered. The obtained solid was dried under a reduced pressure to give 47 mg (0.092 mmol) of an orange-colored solid (complex C-3). The yield was 28%.

FAB-MASS: m/z 473 ($M^+$-Cl), 437 ($M^+$-2Cl), 374 ($M^+$-$CuCl_2$).

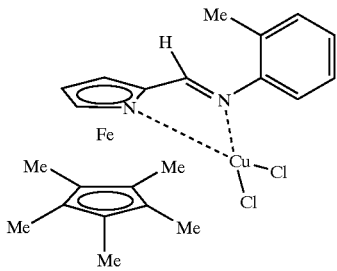

EXAMPLE 15

Synthesis of Complex C-4

Synthesis of Precursor Compound

The atmosphere within a 100 ml Schlenk flask was replaced with nitrogen, and, 255 mg (2.01 mmol) of iron(II) chloride and 10 ml of THF were placed therein. The atmosphere within a 50 ml Schlenk flask was replaced with nitrogen, and, 785 mg (1.75 mmol) of pentaphenylcyclopentadiene and 20 ml of THF were placed in therein. Then 1.24 ml of a 1.56M (1.93 mmol) n-BuLi solution in hexane was dropwise added at room temperature into the 50 ml flask, followed by stirring for 5 minutes. The thus-obtained solution was introduced in the slurry of iron(II) chloride in THF by using cannula. Then a solution of 216 mg (2.05 mmol) of potassium pyrrolide in 10 ml of THF was introduced by using a cannula. The mixture was stirred at room temperature for 2 hours to effect a reaction, and then 15 ml of water was added to quench the reaction liquid. The reaction liquid was extracted with 25 ml of dichloromethane and the obtained organic phase was concentrated under a reduced pressure. The residue was purified by a silica gel column chromatography (solvent: dichloromethane, ethyl acetate) to give 868 mg (1.53 mmol) of an orange solid (1',2',3',4',5'-pentaphenyl-azaferrocene). The yield was 87%.

$^1$H-NMR (400 MHz, $CD_2Cl_2$) δ=4.71 (t, J=0.7 Hz, 2H), 5.44 (t, J=0.7 Hz, 2H), 7.07–7.12 (m, 10H), 7.14–7.20 (m, 15H).

Synthesis of Coordinative Compound

The atmosphere within a 50 ml Schlenk flask was replaced with nitrogen, and, 985 mg (1.73 mmol) of 1',2', 3',4',5'-pentaphenylazaferrocene was dissolved in 21 ml of THF in the flask. The solution was cooled to −50° C. and 2.35 ml of a 1.59M (3.74 mmol) n-BuLi solution in hexane was dropwise added. Then the mixture was stirred at −50° C. for 3 hours and then 284 mg (3.89 mmol) of N,N-dimethylformamide was added. A reaction was carried out for 40 minutes while the temperature was gradually elevated, and then water was added to quench the reaction liquid. The reaction liquid was extracted with ether and the obtained organic phase was concentrated under a reduced pressure. The residue was purified by a silica gel column chromatography (solvent: hexane/dichloromethane, ethyl acetate) to give 743 mg (1.25 mmol) of an orange liquid. The yield was 72%.

The atmosphere within a 50 ml Schlenk flask was replaced with nitrogen, and, 92 mg (0.15 mmol) of the 2-formylazaferrocene prepared by the above-mentioned procedures and 4 ml of ethanol were placed therein. Then 25 mg (0.23 mmol) of o-toluidine and 5 mg of acetic acid were added. A reaction was effected at room temperature for one day, and then, the reaction liquid was concentrated under a reduced pressure. The residue was washed with hexane and dried under a reduced pressure to give 76 mg (0.11 mmol) of a red solid (coordinative compound). The yield was 73%.

$^1$H-NMR (400 MHz, $C_6D_6$) δ=2.31 (s, 3H), 4.48 (s, 1H), 5.45 (s, 1H), 5.55 (s, 1H), 6.14 (d, J=7.0 Hz, 1H), 6.78–7.06 (m, 18H), 7.42 (d, J=6.2 Hz, 10H), 8.44 (s, 1H).

Synthesis of Complex C-4

The atmosphere within a 50 ml Schlenk flask was replaced with nitrogen, and, the flask was charged with 20 mg (0.065 mmol) of (DME)$NiBr_2$ and 2 ml of dichloromethane. With stirring, a solution of 40 mg (0.058 mmol) of the coordinative compound, prepared by the above-mentioned procedures, in 3 ml of dichloromethane, was added by using a cannula. The mixture was stirred at room temperature for 3 hours, and the reaction liquid was filtered and then, extracted with dichloromethane. The combined dichloromethane solutions were concentrated under a reduced pressure. The residue was washed with hexane, and then dried under a reduced pressure to give 44 mg (0.048 mmol) of a reddish brown solid (complex C-4). The yield was 83%.

FAB-MASS: m/z 823 ($M^+$-Br), 743 ($M^+$-2Br), 684 ($M^+$-$NiBr_2$).

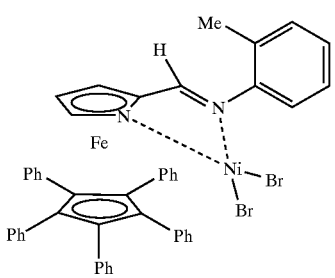

EXAMPLE 16

Synthesis of Complex C-5

Synthesis of Coordinative Compound

The atmosphere within a 50 ml Schlenk flask was replaced with nitrogen, and, 291 mg (0.49 mmol) of 1',2',3',4',5'-pentaphenyl-2-formylazaferrocene was dissolved in 10 ml of ethanol in the flask. Then 86 mg (0.64 mmol) of 2-isopropylaniline and 10 mg of acetic acid were added. The mixture was stirred at room temperature for 2 days, and then, the reaction liquid was concentrated under a reduced pressure. The residue was washed with a minor amount of ethanol, and dried under a reduced pressure to give 289 mg (0.41 mmol) of a red solid (coordinative compound). The yield was 83%.

$^1$H-NMR (400 MHz, $C_6D_6$) δ=1.16 (d, J=6.4 Hz, 3H), 1.31 (d, J=6.4 Hz, 3H), 3.65–3.78 (m, 1H), 4.46 (s, 1H), 5.47 (s, 1H), 5.55 (s, 1H), 6.01 (d, J=7.0 Hz, 1H), 6.78–7.04(m, 18H), 7.40 (d, J=6.2 Hz, 10H), 8.49 (s, 1H).

Synthesis of Complex C-5

The atmosphere within a 50 ml Schlenk flask was replaced with nitrogen, and, the flask was charged with 56 mg (0.18 mmol) of (DME)NiBr$_2$ and 2 ml of dichloromethane. With stirring, a solution of 129 mg (0.18 mmol) of the coordinative compound, prepared by the above-mentioned procedures, in 6 ml of dichloromethane, was added by using a cannula. The mixture was stirred at room temperature for 3 hours, and the reaction liquid was concentrated under a reduced pressure. The residue was washed with a minor amount of dichloromethane, and dried under a reduced pressure to give 160 mg (0.17 mmol) of a red solid (complex C-5). The yield was 95%.

FAB-MASS: m/z 712 (M$^+$-NiBr$_2$).

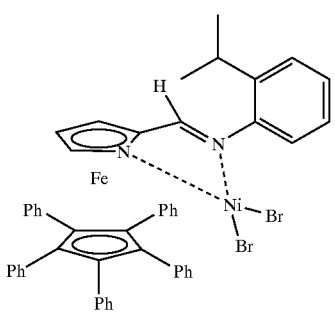

EXAMPLE 17

Synthesis of Complex C-6

Synthesis of Coordinative Compound

The atmosphere within a 50 ml Schlenk flask was replaced with nitrogen, and, 132 mg (0.22 mmol) of 1',2',3',4',5'-pentaphenyl-2-formylazaferrocene was dissolved in 6 ml of ethanol in the flask. Then 49 mg (0.29 mmol) of 2-aminobiphenyl and 5 mg of acetic acid were added. The mixture was stirred at room temperature for 2 days, and then, the reaction liquid was concentrated under a reduced pressure. The residue was washed with a minor amount of ethanol, and dried under a reduced pressure to give 122 mg (0.16 mmol) of a red solid (coordinative compound). The yield was 74%.

$^1$H-NMR (400 MHz, $C_6D_6$) δ=4.39 (s, 1H), 5.29 (s, 1H), 5.51 (s, 1H), 6.99 (d, J=7.6 Hz, 1H), 6.80–7.10 (m, 18H), 7.12–7.20 (m, 3H), 7.36 (d, J=7.0 Hz, 10H), 7.51 (d, J=7.0 Hz, 2H), 8.53 (s, 1H).

Synthesis of Complex C-6

The atmosphere within a 50 ml Schlenk flask was replaced with nitrogen, and, the flask was charged with 40 mg (0.13 mmol) of (DME)NiBr$_2$ and 2 ml of dichloromethane. With stirring, a solution of 105 mg (0.14 mmol) of the coordinative compound, prepared by the above-mentioned procedures, in 5 ml of dichloromethane, was added by using a cannula. The mixture was stirred at room temperature for 3 hours, and the reaction liquid was concentrated under a reduced pressure. The residue was washed with hexane, and dried under a reduced pressure to give 110 mg (9.11 mmol) of a red solid (complex C-6). The yield was 85%.

FAB-MASS: m/z 885 (M$^+$-Br), 805 (M$^+$-2Br), 747 (M$^+$-NiBr$_2$).

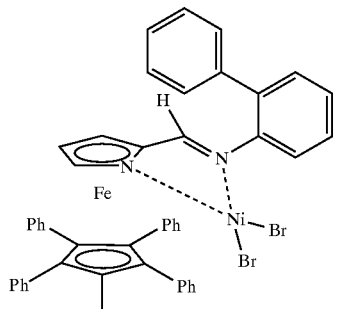

EXAMPLE 18

Synthesis of Precursor Compound

By the method described in Chem. Commun., p1889 (1998), 1',2',3',4',5'-penta(p-fluorophenyl)cyclopentadiene was synthesized.

The procedures for synthesizing the precursor compound described in Example 15 were repeated wherein 1',2',3',4',5'-penta(p-fluorophenyl)cyclopentadiene was used instead of 1',2',3',4',5'-pentaphenylcyclopentadiene with all other conditions remaining the same. Thus an orange-colored solid, 1',2',3',4',5'-penta(p-fluorophenyl)azaferrocene was obtained in a yield of 47%.

$^1$H-NMR (400 MHz, $C_6D_6$) δ=4.08 (d, J=0.8 Hz, 2H), 5.10 (t, J=0.8 Hz, 2H), 6.58–6.68 (m, 10H), 7.00–7.10 (m, 10H).

EXAMPLE 19

Synthesis of Precursor Compound

By the method described in Chem. Commun., p1889 (1998), 1',2',3',4',5'-penta(p-methoxyphenyl) cyclopentadiene was synthesized.

The procedures for synthesizing the precursor compound described in Example 15 were repeated wherein 1',2',3',4',5'-penta(p-methoxyphenyl)cyclopentadiene was used instead of 1',2',3',4',5'-pentaphenylcyclopentadiene with all other conditions remaining the same. Thus an orange-colored solid, 1',2',3',4',5'-penta(p-methoxyphenyl) azaferrocene was obtained in a yield of 72%.

$^1$H-NMR (400 MHz, $C_6D_6$) δ=3.23 (s, 15H), 4.47 (s, 2H), 5.48 (s, 2H), 6.60 (d, J=8.8 Hz, 10H), 7.40 (d, J=8.8 Hz, 10H).

EXAMPLE 20

Preparations of Complex Solution

The atmosphere within a 100 ml of Schlenk flask was replaced with nitrogen, and the flask was charged with 28 mg (47 μmol) of complex C-1 synthesized in Example 12, and 50 ml of toluene. The content was stirred for 20 minutes to prepare a complex solution.

Polymerization of Ethylene

Two liter autoclave war charged with 500 ml of toluene, and methylaluminoxane (PMAO available from Tosoh Akzo K.K., in an amount of 1.6 ml [equivalent to 4.6 mmol of aluminum atom]). Ethylene was blown therein to a pressure of 10 kg/cm$^2$G. The complex solution prepared by the above-mentioned procedure was pressed into the autoclave at room temperature, and polymerization was carried out for 1 hour while ethylene was continuously fed therein at a rate such that the pressure of 10 kg/cm$^2$G was maintained, Methanol was pressed into the autoclave to quench the polymerization liquid, and the pressure was released. Methanol was further added to precipitate a polymer. The polymer was filtered and then washed with methanol. The polymer was dried under a reduced pressure to give 82.7 g of a solid polymer. The activity was 1.7 kg/Ni·mmol·h. Analysis by differential scanning calorimeter (DSC) revealed that the polymer had a melting point of 77.5° C. GPC (1,2,4-trichlorobenzene, 140° C.) revealed that the polymer had Mw of 1.0×10$^4$ and a molecular weight distribution (Mw/Mn) of 2.2.

EXAMPLE 21–24

The procedures described in Example 20 were repeated wherein the transition metal compounds and polymerization temperatures, shown in Table 1, were employed with all other conditions remaining the same. The evaluation results of the polymers are shown in Table 1.

TABLE 1

| Example No. | 20 | 21 | 22 | 23 | 24 |
|---|---|---|---|---|---|
| Complex | C-1 | C-1 | C-4 | C-5 | C-6 |
| Amount of complex (μmol) | 47 | 20 | 25 | 24 | 22 |
| Polymerization temperature | Room temp. | 50° C. | Room temp. | Room temp. | Room temp. |
| Yield of polymer (g) | 82.7 | 26.4 | 77.5 | 94.8 | 25.2 |
| Activity (kg/Ni · mmol · h) | 1.7 | 1.3 | 3.1 | 3.9 | 1.1 |
| GPC Mw (×10$^4$) | 1.0 | 1.5 | 6.3 | 11.0 | 4.1 |
| Mw/Mn | 2.2 | 3.6 | 4.9 | 4.5 | 2.5 |
| DSC melting point (° C.) | 77.5 | — | 39.9 | 31.0 | 89.0 |

Al/Ni = 100 (mol ratio), polymerization time: 1 hour

EXAMPLE 25

Preparation of Complex Solution

The atmosphere within a 100 ml of Schlenk flask was replaced with nitrogen, and the flask was charged with 52 mg (0.056 mmol) of complex C-5 synthesized in Example 16, and 60 ml of toluene. The content was stirred for 20 minutes to prepare a complex solution.

Copolymerization of Ethylene/Methyl Acrylate

Two liter autoclave was charged with 450 ml of toluene, and methylaluminoxane (PMAO available from Tosoh Akzo K.K., in an amount of 2.0 ml [equivalent to 5.7 mmol of aluminum atom]). Ethylene was blown therein to a pressure of 1 kg/cm$^2$G. The complex solution prepared by the above-mentioned procedure was pressed into the autoclave, and the mixture was stirred for 5 minutes. Then a solution of 5 ml (56 mmol) of methyl acrylate and 0.5 ml of methylaluminoxane in 40 ml of toluene was pressed into the autoclave, and then polymerization was carried out at room temperature for 27 hours while ethylene was continuously fed therein at a rate such that the pressure of 5 kg/cm$^2$G was maintained. The thus-obtained reaction liquid was quenched with 350 ml of 0.1N hydrochloric acid, and separated into two phases. The organic phase was washed with water and filtered, and then, the filtrate was concentrated under a reduced pressure to give 4.0 g of a rubbery viscous solid copolymer.

$^1$H-NMR (CDCl$_3$) revealed that the content of methyl acrylate units in the copolymer was 7% by weight.

EXAMPLE 26

Synthesis of Complex C-7

The atmosphere within a 100 ml Schlenk flask was replaced with nitrogen, and, 152 mg (0.21 mmol) of the coordinate compound prepared in Example 16 and 55.4 mg (0.21 mmol) of (1,5-cyclooctadiene)Pd(Me)Cl were placed therein. 12 ml of diethyl ether was added, and the mixture was stirred at room temperature for 3 hours. A supernatant was removed and the residue was washed with 6 ml of diethyl ether. The obtained solid was dried to give 166 mg (0.19 mmol) of a pink-colored solid (complex C-7). The yield was 92%.

$^1$H-NMR (400 MHz, CD$_2$Cl$_2$) δ=0.40 (s, 3H), 0.86 (d, J=6.6 Hz, 3H), 1.26 (d, J=6.6 Hz, 3H), 3.34–3.50 (m, 1H), 5.29 (s, 1H), 5.35 (s, 1H), 5.84 (s, 1H), 5.90 (d, J=8.4 Hz, 1H), 6.93–7.44 (m, 28H), 8.23 (s, 1H).

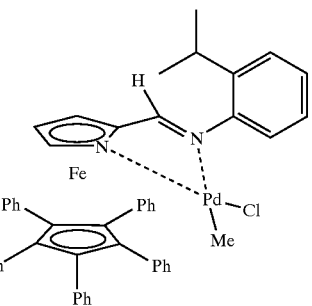

EXAMPLE 27

Synthesis of Complex C-8

The atmosphere within a 50 ml Schlenk flask was replaced with nitrogen, and, 71 mg (0.082 mmol) of the transition metal compound synthesized in Example 26 and 29 mg (0.085 mmol) of AgSbF$_6$ were placed therein. The mixture was cooled to −50° C. and 8 ml of diethyl ether was added. A cooling bath was removed, and the mixture was stirred at room temperature for 1 hour. The reaction liquid was filtered, and the residue was extracted with 16 ml of a dichloromethane/diethyl ether (1:1) mixed solution. The extract was combined with the above-mentioned filtrate. The combined liquid was concentrated to 10 ml under a reduced pressure. Then 20 ml of hexane was added to precipitate a solid. A supernatant was removed, and the obtained solid was dried to give 76 mg of a reddish-brown sold (complex C-8). The yield was 81%.

$^1$H-NMR (400 MHz, $CD_3CN$) δ=1.13 (t, J=7.0 Hz, 6H), 1.20 (s, 1.5H), 1.22 (s, 1.5H), 2.04–2.30 (brs), 3.43 (q, J=7.0 Hz, 4H), 5.72 (d, J=1.5 Hz, 1H), 5.81 (d, J=2.5 Hz, 1H), 6.08 (s, 1H), 6.26 (d, J=7.7 Hz, 1H), 7.00–7.37 (m, 28H), 8.80 (s, 1H).

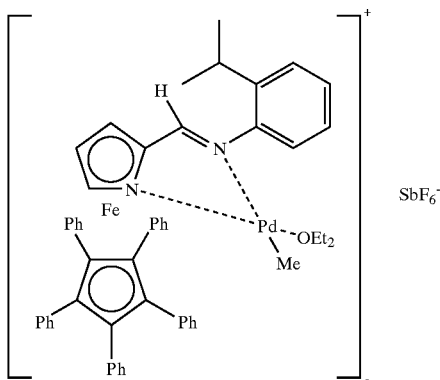

What is claimed is:

1. A transition metal compound represented by the following formula (1):

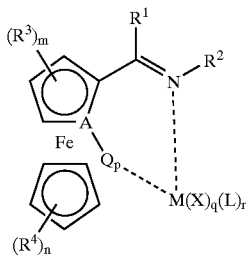

(1)

wherein M represents a transition metal atom selected from the group consisting of metal atoms of group 3 to group 12 of the periodic table;

X represents a hydrogen atom, a halogen atom, a hydrocarbon group having 1 to 20 carbon atoms, a hydrocarbyloxygroup having 1 to 20 carbon atoms, an amino group having one or more hydrocarbon groups each with 1 to 20 carbon atoms, a sulfonate group having an organic residue with 1 to 20 carbon atoms, or a non-coordinative anion containing an element selected from the group consisting of B, Al, P and Sb, and, when q is an integer of at least 2, Xs may be the same as or different from each other;

A represents a carbon atom, a nitrogen atom or a phosphorus atom;

$R^1$ represents a hydrogen atom, a hydrocarbon group having 1 to 20 carbon atoms, a hydrocarbon group having 1 to 20 carbon atoms and containing at least one halogen atom, or a ferrocenyl group or a substituted ferrocenyl group;

$R^2$ represents a hydrogen atom, a hydrocarbon group having 1 to 20 carbon atoms, a hydrocarbon group having 1 to 20 carbon atoms and containing at least one atom selected from the group consisting of halogen, silicon, nitrogen, oxygen and sulfur atoms, or a ferrocenyl group or a substituted ferrocenyl group; and $R^1$ and $R^2$ may form together a ring;

Q represents a hydrogen atom, a hydrocarbon group having 1 to 20 carbon atoms, a silyl group having one or more hydrocarbon groups each with 1 to 20 carbon atoms, an amino group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, a hydrocarbon group having 1 to 20 carbon atoms and containing at least one atom selected from the group consisting of nitrogen, phosphorus, oxygen and sulfur atoms, or oxygen or sulfur; and, when Q contains a coordinative atom, Q can be coordinatively bound to M;

$R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from the group consisting of nitrogen, oxygen, halogen and sulfur atoms and one of $R^3$s adjacent to Q may form a ring together with Q; and, when m is an integer of at least 2, $R^3$s may be the same as or different from each other, and adjacent $R^3$s may form together a ring;

$R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from the group consisting of nitrogen, phosphorus, oxygen, halogen and sulfur atoms; and, when n is an integer of at least 2, $R^4$s may be the same as or different from each other, and adjacent $R^4$s may form together a ring; and $R^3$ and $R^4$ may form together a ring; and, when $R^4$ contains a heteroatom, $R^4$ can coordinate with the transision metal atom M;

L is a coordinate bond-forming compound selected from the group consisting of π electron, ethers, nitriles, anilines and phosphines, and L may be bound to X;

m is an integer of 1 to 3, n is an integer of 1 to 5, and p is an integer of 0 or 1;

when Q is sulfur or oxygen, the bond between Q and M is a sigma bond;

when p is 0 and A is a nitrogen atom or a phosphorus atom, A can be coordinatively bound to M; and q is an integer of 1 to 3 and r is an integer of 0 to 3.

2. A transition metal compound represented by the following formula (2):

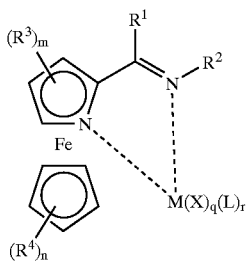 (2)

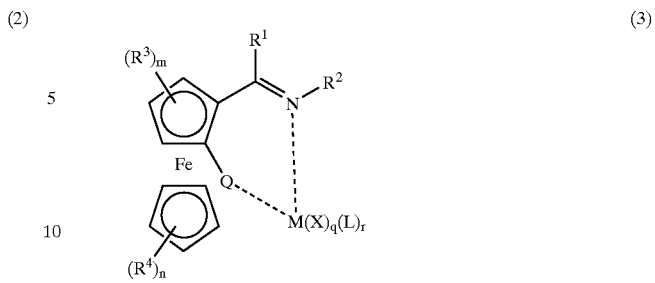 (3)

wherein M represents a transition metal atom selected from the group consisting of metal atoms of group 3 to group 12 of the periodic table;

X represents a hydrogen atom, a halogen atom, a hydrocarbon group having 1 to 20 carbon atoms, a sulfonate group having an organic residue with 1 to 20 carbon atoms, or a non-coordinative anion containing an element selected from the group consisting of B, Al, P and Sb, and, when q is an integer of at least 2, Xs may be the same as or different from each other;

$R^1$ represents a hydrogen atom, a hydrocarbon group having 1 to 20 carbon atoms, a hydrocarbon group having 1 to 20 carbon atoms and containing at least one halogen atom, or a ferrocenyl group or a substituted ferrocenyl group;

$R^2$ represents a hydrogen atom, a hydrocarbon group having 1 to 20 carbon atoms, a hydrocarbon group having 1 to 20 carbon atoms and containing at least one atom selected from the group consisting of halogen, silicon, nitrogen, oxygen and sulfur atoms, or a ferrocenyl group or a substituted ferrocenyl group; and $R^1$ and $R^2$ may form together a ring;

$R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from the group consisting of nitrogen, oxygen, halogen and sulfur atoms and, when m is an integer of at least 2, $R^3$s may be the same as or different from each other, and adjacent $R^3$s may form together a ring;

$R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from the group consisting of nitrogen, phosphorus, oxygen, halogen and sulfur atoms; and, when n is an integer of at least 2, $R^4$s may be the same as or different from each other, and adjacent $R^4$s may form together a ring; and $R^3$ and $R^4$ may form together a ring;

L is a coordinate bond-forming compound selected from the group consisting of π electron, ethers, nitriles, amines and phosphines, and L may be bound to X;

m is an integer of 1 to 3, n is an integer of 1 to 5, q is an integer of 1 to 3 and r is an integer of 0 to 3.

3. A transition metal compound represented by the following formula (3):

wherein M represents a transition metal atom selected from the group consisting of metal atoms of group 3 to group 12 of the periodic table;

X represents a hydrogen atom, a halogen atom, a hydrocarbon group having 1 to 20 carbon atoms, a hydrocarbyloxygroup having 1 to 20 carbon atoms, an amino group having one or more hydrocarbon groups each with 1 to 20 carbon atoms, a sulfonate group having an organic residue with 1 to 20 carbon atoms, or a non-coordinative anion containing an element selected from the group consisting of B, Al, P and Sb, and, when q is an integer of at least 2, Xs may be the same as or different from each other;

$R^1$ represents a hydrogen atom, a hydrocarbon group having 1 to 20 carbon atoms, a hydrocarbon group having 1 to 20 carbon atoms and containing at least one halogen atom, or a ferrocenyl group or a substituted ferrocenyl group;

$R^2$ represents a hydrogen atom, a hydrocarbon group having 1 to 20 carbon atoms, a hydrocarbon group having 1 to 20 carbon atoms and containing at least one atom selected from the group consisting of halogen, silicon, nitrogen, oxygen and sulfur atoms, or a ferrocenyl group or a substituted ferrocenyl group; and $R^1$ and $R^2$ may form together a ring;

Q represents a hydrogen atom, a hydrocarbon group having 1 to 20 carbon atoms, a silyl group having one or more hydrocarbon groups each with 1 to 20 carbon atoms, an amino group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, a hydrocarbon group having 1 to 20 carbon atoms and containing at least one atom selected from the group consisting of nitrogen, phosphorus, oxygen and sulfur atoms, or oxygen or sulfur; and, when Q contains a coordinative atom, Q can be coordinatively bound to M;

$R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from the group consisting of nitrogen, oxygen, halogen and sulfur atoms, and one of $R^3$s adjacent to Q may form a ring together with Q; and, when m is an integer of at least 2, $R^3$s may be the same as or different from each other, and adjacent $R^3$s may form together a ring;

$R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from the group consisting of nitrogen, phosphorus, oxygen, halogen and sulfur atoms; and, when n is an integer of at least 2, $R^4$s may be the same as or different from each other, and adjacent $R^4$s may form together a ring; and $R^3$ and $R^4$ may form together a ring; and, when $R^4$ contains a heteroatom, $R^4$ can coordinate with the transision metal atom M;

L is a coordinate bond-forming compound selected from the group consisting of π electron, ethers, nitriles, amines and phosphines, and L may be bound to X;

m is an integer of 1 to 3 and n is an integer of 1 to 5;

when Q is sulfur or oxygen, the bond between Q and M is a sigma bond; and q is an integer of 1 to 3 and r is an integer of 0 to 3.

4. A transition metal compound represented by the following formula (4):

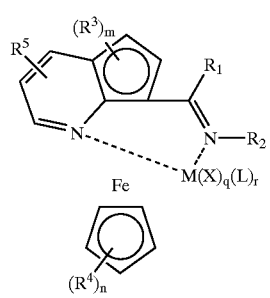

(4)

wherein M represents a transition metal atom selected from the group consisting of metals of group 3 to group 12 of the periodic table;

X represents a hydrogen atom, a halogen atom, a hydrocarbon group having 1 to 20 carbon atoms, a sulfonate group having an organic residue with 1 to 20 carbon atoms, or a non-coordinative anion containing an element selected from the group consisting of B, Al, P and Sb, and, when q is an integer of at least 2, Xs may be the same as or different from each other;

$R^1$ represents a hydrogen atom, a hydrocarbon group having 1 to 20 carbon atoms, a trifluoromethyl group, a ferrocenyl group or a substituted ferrocenyl group;

$R^2$ represents a hydrogen atom, a hydrocarbon group having 1 to 20 carbon atoms, a hydrocarbon group having 1 to 20 carbon atoms and containing at least one atom selected from the group consisting of silicon, nitrogen, oxygen and sulfur atoms, or a ferrocenyl group or a substituted ferrocenyl group; and $R^1$ and $R^2$ may form together a ring;

$R^3$ represents a hydrogen atom, a hydrocarbon group having 1 to 20 carbon atoms or a silyl group having one or more hydrocarbon groups each with 1 to 20 carbon atoms; and, when m is an integer of at least 2, $R^3$s may be the same as or different from each other;

$R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from the group consisting of nitrogen, phosphorus, oxygen, halogen and sulfur atoms; and, when n is an integer of at least 2, $R^4$s may be the same as or different from each other, and adjacent $R^4$s may form together a ring;

$R^5$ represents a hydrogen atom, a hydrocarbon group having 1 to 20 carbon atoms or an amino group having one or more hydrocarbon groups each with 1 to 20 carbon atoms;

L is a coordinate bond-forming compound selected from the group consisting of π electron, ethers, nitriles, amines and phosphines, and L may be bound to X;

m is an integer of 1 or 2, n is an integer of 1 to 5, q is an integer of 1 to 3 and r is an integer of 0 to 3.

5. The transition metal compound according to any one of claims 1 to 4, wherein M represents a transition metal atom selected from the group consisting of metal atoms of group 8 to group 12 of the periodic table.

6. The transition metal compound according to any one of claims 1 to 4, wherein M represents a transition metal atom selected from the group consisting of Ni, Pd, Fe and Cu.

7. A coordinative compound represented by the following formula (5):

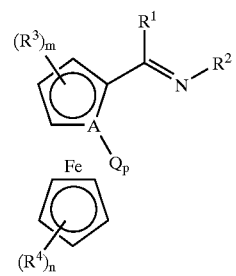

(5)

wherein A represents a carbon atom, a nitrogen atom or a phosphorus atom;

$R^1$ represents a hydrogen atom, a hydrocarbon group having 1 to 20 carbon atoms, a hydrocarbon group having 1 to 20 carbon atoms and containing at least one halogen atom, or a ferrocenyl group or a substituted ferrocenyl group;

$R^2$ represents a hydrogen atom, a hydrocarbon group having 1 to 20 carbon atoms, a hydrocarbon group having 1 to 20 carbon atoms and containing at least one atom selected from the group consisting of halogen, silicon, nitrogen, oxygen and sulfur atoms, or a ferrocenyl group or a substituted ferrocenyl group; and $R^1$ and $R^2$ may form together a ring;

Q represents a hydrogen atom, a hydrocarbon group having 1 to 20 carbon atoms, a silyl group having one or more hydrocarbon groups each with 1 to 20 carbon atoms, an amino group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, a hydrocarbon group having 1 to 20 carbon atoms and containing at least one atom selected from the group consisting of nitrogen, phosphorus, oxygen and sulfur atoms, or a hydroxyl group or a thiol group;

$R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from the group consisting of nitrogen, oxygen, halogen and sulfur atoms and one of $R^3$s adjacent to Q may form a ring together with Q; and, when m is an integer of at least 2, $R^3$s may be the same as or different from each other, and adjacent $R^3$s may form together a ring;

$R^4$ represents a hydrogen atom, a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from the group consisting of nitrogen, phosphorus, oxygen, halogen and sulfur atoms; and, when n is an integer of at least 2, $R^4$s may be the same as or different from each other, and adjacent $R^4$s may form together a ring; and $R^3$ and $R^4$ may form together a ring; and m is an integer of 1 to 3, n is an integer of 1 to 5, and p is an integer of 0 or 1.

8. A compound which is a precursor to the coordinative compound represented by formula (5) shown in claim 7, and which is represented by the following formula (6):

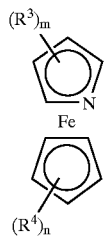

(6)

wherein $R^3$ represents a hydrogen atom, a halogen atom, a hydrocarbon group having 1 to 20 carbon atoms, a silyl group having one or more hydrocarbon groups each with 1 to 20 carbon atoms, or a hydrocarbon group having 1 to 20 carbon atoms and containing at least one atom selected from the group consisting of nitrogen, oxygen, halogen and sulfur atoms and, when m is an integer of at least 2, $R^3$s may be the same as or different from each other, and adjacent $R^3$s may form together a ring;

$R^4$ represents a hydrocarbon group having 1 to 20 carbon atoms, a silyl group having one or more hydrocarbon groups each with 1 to 20 carbon atoms, a phosphino group having one or more hydrocarbon groups each with 1 to 20 carbon atoms, an oxy group having a hydrocarbon group with 1 to 20 carbon atoms, a thio group having a hydrocarbon group with 1 to 20 carbon atoms, or a hydrocarbon group having 1 to 20 carbon atoms and containing at least one atom selected from the group consisting of nitrogen, phosphorus, oxygen, halogen and sulfur atoms; and, when n is an integer of 1, $R^4$ is not a methyl group; and when n is an integer of at least 2, $R^4$s may be the same as or different from each other, and all of the $R^4$s are not simultaneously a methyl group; and adjacent $R^4$s may form together a ring; and $R^3$ and $R^4$ may form together a ring; and m is an integer of 1 to 3 and n is an integer of 1 to 5.

9. A catalyst for polymerization of an olefin, which comprises the transition metal compound as claimed in any one of claims 1 to 4.

10. A catalyst for polymerization of an olefin, which comprises the transition metal compound as claimed in any one of claims 1 to 4, and an activating cocatalyst.

11. A process for polymerization of an olefin, which comprises polymerizing an olefin in the presence of a catalyst comprising the transition metal compound as claimed in any one of claims 1 to 4.

12. A process for polymerization of an olefin, which comprises polymerizing an olefin in the presence of a catalyst comprising the transition metal compound as claimed in any one of claims 1 to 4, and an activating cocatalyst.

* * * * *